(12) United States Patent
Tsitouras

(10) Patent No.: US 10,463,521 B2
(45) Date of Patent: Nov. 5, 2019

(54) SHOE-INTERNAL BRACE FOR DROP FOOT AND SIMILAR CONDITIONS

(71) Applicant: Andreas Tsitouras, Nea Smyrni (GR)

(72) Inventor: Andreas Tsitouras, Nea Smyrni (GR)

( * ) Notice: Subject to any disclaimer, the term of this patent is extended or adjusted under 35 U.S.C. 154(b) by 850 days.

(21) Appl. No.: 14/784,369

(22) PCT Filed: Apr. 15, 2013

(86) PCT No.: PCT/GR2013/000019
§ 371 (c)(1),
(2) Date: Oct. 14, 2015

(87) PCT Pub. No.: WO2014/170700
PCT Pub. Date: Oct. 23, 2014

(65) Prior Publication Data
US 2016/0058595 A1    Mar. 3, 2016

(51) Int. Cl.
*A61F 5/14*      (2006.01)
*A61F 5/01*      (2006.01)

(52) U.S. Cl.
CPC ................... *A61F 5/0113* (2013.01)

(58) Field of Classification Search
CPC .... A61F 5/0113; A61F 5/0111; A61F 5/0125; A61F 5/0127
USPC ................................ 602/26–27, 28
See application file for complete search history.

(56) References Cited

U.S. PATENT DOCUMENTS

| | | | | |
|---|---|---|---|---|
| 3,779,654 A * | 12/1973 | Horne | ..................... | A61F 2/582 403/62 |
| 4,934,355 A * | 6/1990 | Porcelli | ................. | A61F 5/0127 602/16 |
| 5,449,005 A * | 9/1995 | Echols | ..................... | A43B 7/20 128/882 |
| 5,620,413 A * | 4/1997 | Olson | ................... | A61F 5/0111 602/27 |
| 6,824,523 B2 * | 11/2004 | Carlson | ................. | A61F 5/0113 602/16 |
| 7,112,180 B2 * | 9/2006 | Guenther | .............. | A61F 5/0111 128/882 |
| 8,048,012 B1 * | 11/2011 | Castro | ................... | A61F 5/0127 602/23 |

* cited by examiner

*Primary Examiner* — Kari K Rodriquez
*Assistant Examiner* — Camtu T Nguyen

(57) ABSTRACT

An orthopedic brace for drop foot correction comprising a foot base portion (1) pivotally connected to a calf covering portion (2) by means of sole-raising hinge assemblies, comprising metallic strip members (3,3') with openings (31) and metallic plate members preferably with openings (41), wherein members (3, 3') are fixedly embedded within flanges (1a,1b) of the foot base portion (1) and members (4) are fixedly embedded within flanges (2a,2b) of the calf covering portion (2) during the injection thermosetting process of manufacturing the brace, as openings (31,41) are filled with plastic raw material. The brace is provided in distinct sizes as a ready to wear product and comprises a strap fastener profile (6) that securely fastens the calf covering portion onto the leg of the user and provides correction varus/valgus type structural misalignment of the foot of the user when passed through an aperture (20) located proximately the bottom of the calf covering portion.

13 Claims, 16 Drawing Sheets

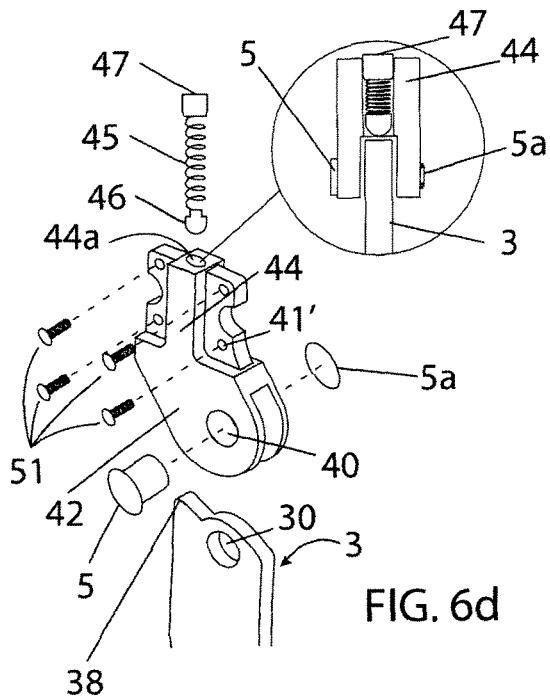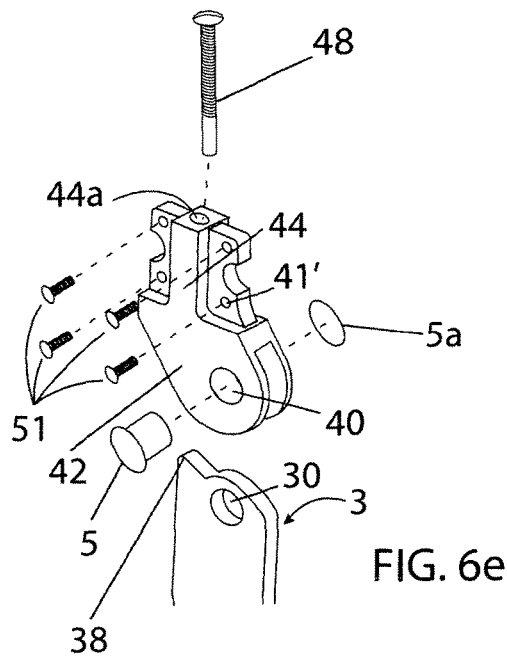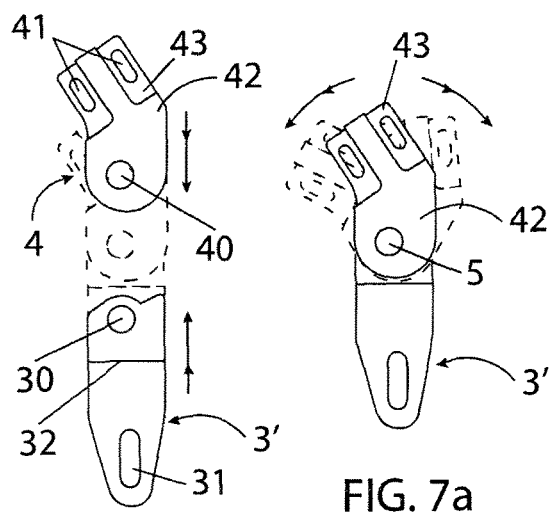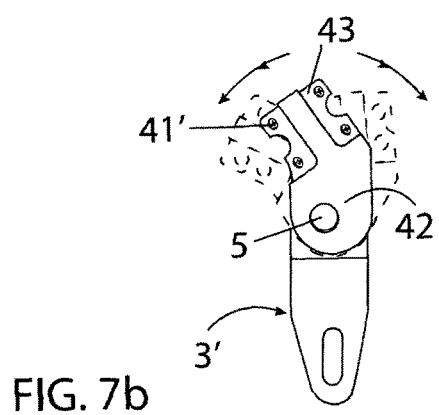

SHOE-INTERNAL BRACE FOR DROP FOOT AND SIMILAR CONDITIONS

THE FIELD OF THE ART

The invention relates generally to braces particularly adapted to provide foot raising assistance to drop foot patients and proposes a ready-to-wear drop foot correcting brace that can be readily worn, subjected to trial and immediate purchase.

BACKGROUND OF THE INVENTION

Drop foot is a deficit in turning the ankle and toes upward. The individual with drop foot experiences a difficulty in raising the foot, such condition being due to damage in the deep fibular/peroneal nerve innervating the anterior compartment of the leg and leading to inability of the leg to dorsiflex the foot. Conditions leading to drop foot may be neurologic, muscular or anatomic in origin, often with significant overlap. The result is an abnormal gait. The foot of the patient will hang inferiorly thereby leading to the individual walking with this condition to stumble and sometimes fall when hitting upon the slightest rise in a walk way.

In order to assist drop foot patients to walk properly, i.e. in order to provide dorsiflexion assistance to the foot of the wearer, the calf and the foot ankles can be stabilized by means of specially configured customized braces adapted to assist with drop foot conditions.

A variety of braces particularly adapted to assist with drop foot problems has been developed. Early braces were made of metal and were secured to a modified or customized shoe so as to hold the shoe in a generally horizontal, however uncomfortably rigid position for supporting the foot. Later on, braces accommodated a spring biased platform for supporting the foot and permitted minimal flexing of the foot when walking, thereby creating a more natural movement. With the advent of plastics, molded braces were produced and made available also in an articulating construction, wherein an independently made foot base portion was hingedly connected to a posterior brace item. Whilst such plastic braces were lighter and aesthetically more acceptable than earlier metal braces, they still were distant from successfully simulating normal foot function since the plastic posterior brace item hinged the foot base portion with a single hinge assembly located behind the heel rather than the real life articulation in front of the heel. Further, still braces of this kind necessitated the use of modified or in the least enlarged shoes, generally making the condition and the brace obvious to even the most casual observer.

The creation of a brace that accomplished a pair of hinge assemblies located on either side of the foot proximally to the ankle and at an orientation such as to have the line passing through this pair of hinge assemblies at approximate alignment with the actual axis passing through the malleolus lateralis and malleolus medialis of the talocrural articulation was made necessary in order to have the brace providing simulation of a nearly normal foot function. Such a brace with a bilateral hinge assembly was thus developed as a customized product with such hinge assembly comprising a sole-raising spring mechanism of the malleolus medialis and a sole-raising mechanism of the malleolus lateralis. Each hinge assembly of such a typical customized foot brace adapted to provide ankle-foot-orthosis (AFO) of the prior art comprises two constituent members, a first member appropriately connected at each one of a pair of the rear upwardly extending lateral flanges of the foot base portion of the brace and a second spring loaded member connected at each one of a pair of bottom ends of the calf covering portion, such second spring loaded members being pivotally connected to the first members and acting so as to maintain the foot base portion at a predetermined appropriate angle with respect to the calf covering portion, thereby providing a nearly normal walking performance of the patient wearing the brace. Several bolts are employed in securing each one of the abovementioned first members of the hinge assembly to the upwardly extending lateral flanges of the foot base portion of the brace and further several bolts are employed in securing each one of the abovementioned second members of the hinge assembly to the bottom ends of the corresponding calf portion. This plurality of bolts constitutes a potential source of malfunction as one or more of these bolts may in the course of time become loose thereby adversely affecting the performance of the brace. Further such a plurality of bolts necessarily increases the cost of assembling the brace, leads to inferior aesthetics of the brace, whilst it may also cause discomfort to the user wearing the drop foot correcting brace. Most importantly such a brace adapted to provide ankle-foot-orthosis (AFO) is an expensive customized product and the patient must conform with the undesirable practice of ordering and waiting for delivery of a product without having tried it.

Indeed, under the present practice of customized production of braces, the individual has to order and buy a brace product that is not readily available for trial and therefore he or she has no idea of the assistance this product might offer to him or her. A typical purchase of a brace involves measurements made on the individual patient, a plaster model being developed in accordance to these measurements, the final brace product being thereafter developed to correspond with such plaster brace model. Thus, one has to wait for delivery and yet he may also have to compromise with the employment of heavy and/or aesthetically deficient orthopaedic shoes that will make his problem apparent at first sight.

A variety of prior art orthopedic braces adapted to provide dorsiflexion assistance and handle drop foot problems comprising bilaterally provided hinge assemblies that connect a foot base portion with a calf covering portion at the region of the talocrural articulation are illustratively disclosed in EP 1374810 and US 2002/0188238. These braces present the drawbacks and deficiencies mentioned hereinabove.

A further drawback of drop foot braces of the prior art is that they fail to take into account possible additional malfunctioning of the foot of a drop foot patient that if left unattended can result in getting inferior results from the usage of the drop foot correcting brace per se. In particular foot misalignment can result in many forms of discomfort for the patient. Symptoms known to develop from such misalignment are plantar fasciitis, hammertoes, bunions, achilles tendonitis, and others, such foot misalignment possibly also causing or exacerbating knee, hip or back pain. More particularly, structural misalignment of the foot is generally localized to either the fore foot or the rear foot or combinations of both. These structural abnormalities may be generically classified as either of the varus or valgus type. The valgus abnormality refers specifically to a sole position, or of any part of the foot, wherein the sole is turned outward or is being everted, that is away from the body midline to an abnormal degree, whilst the varus abnormality, on the other hand, is a condition of the sole, or of any part of the foot, wherein the sole is turned inward or is being inverted, that is towards the body midline to an abnormal degree.

Previous prior art devices applicable to a shoe or insole in a shoe that have been designed to correct structural abnormalities of the abovementioned types are known. By way of example, U.S. Pat. Nos. 4,333,472 and 5,345,701 have disclosed such devices. Further, U.S. Pat. No. 7,299,568 discloses an orthopaedic foot device that is to be applied to the human foot, to be disposed in footwear and worn for the correction and/or compensation of specifically identified structural biomechanical abnormalities of the human foot. There is however no provision being made in the prior art to correct foot malfunctioning of the varus or valgus type in association with braces specifically designed to handle drop foot problems.

A first object of the invention with a scope of substantially minimizing the cost of the drop foot correcting orthopedic brace with bilaterally provided sole-raising hinge assemblies is to propose an industrial process of brace manufacturing instead of the customized brace production of the prior art, wherein the brace comprises an injection molding manufactured foot base portion and an injection molding manufactured calf covering portion, wherein the first members of each hinge assembly adapted to be connected at the rear upwardly extending lateral flanges of the foot base portion of the brace are fixedly embedded within such lateral flanges and the second spring loaded members adapted to be connected at each one of a pair of bottom ends of the calf portion are alternatively fixedly embedded within such bottom ends of the calf portion or appropriately bolted thereupon, thereafter said industrially produced foot base portion being connected to said industrially produced calf covering portion through pivotal connection of said first and second member of the bilaterally provided hinge assemblies thereof.

It is a further object of the invention to provide the aforementioned drop foot correcting orthopedic brace with endless screw members replacing the bilaterally provided compression springs of the sole-raising hinge assemblies, wherein the endless screw member advances downwardly as it is being screwed within a cavity provided in the abovementioned otherwise spring loaded member of the calf portion and exerts pressure upon the first hinge assembly member that is embedded within the lateral flanges of the foot base portion, whereby the brace of the invention can be employed with a scope of providing assistance to persons suffering from ippopodia (Pes equinus), a permanent deformation of the foot in plantar flexion, such ippopodia corrective assistance especially being used during night resting.

It is a further object of the invention to propose a shoe-internal brace, and in particular an ankle-foot orthosis (AFO) and a knee-ankle-foot orthosis (KAFO) brace product that will be offered ready to wear so that a potential client may readily try the brace before proceeding to buying the same at his full satisfaction.

It is further an object of the invention to provide such ready-to-wear braces at a substantially lower cost than that of customized braces of the prior art, yet providing a fully satisfactory performance in accomplishing the scope of drop foot correction and enable a comfortable use for each individual customer patient.

A further object of the invention is to provide a sufficiently necessary range of distinctly sized braces with appropriately sized foot base portions and correspondingly sized calf covering portions to fit most patients in need of a brace adapted to provide a drop foot correcting capacity wherein a potential customer is provided with a variety of such distinctly sized braces amongst which he or she may choose the appropriately sized brace and readily wear it to fit his or her particular requirements.

It is a further object of the invention to provide the aforementioned brace in a form appropriate for fitting within ordinary shoes thereby providing aesthetic approval and a capacity of the customer patient to wear a plurality of different ordinary shoes with the brace remaining un-noticeable even from the most attentive observers.

It is a further object of the invention to provide the aforementioned calf covering portion of the brace with a pair of an upper and a lower strap fastener profiles that cooperate in providing a firm adjustment of the brace onto the leg of each individual user.

It is a further object of the invention taking into account possible mobility deficiencies of the right or of the left side of each individual user to provide handy usage of the abovementioned upper strap fastener profile of the calf covering portion with either clockwise or anticlockwise rotation of the strap around the calf covering portion of the leg of the user.

It is a further object of the invention to provide handy usage of the abovementioned lower strap fastener profile of the calf covering portion with a scope of providing correction of structural misalignment of the foot of either the varus or the valgus type.

Another object of the invention is to provide alternative embodiments of the aforementioned ready to wear brace, such brace comprising a foot base portion articulated to a leg covering portion extending either all along the shank bone of the calf or extending further upwardly along the femur.

A further object of the invention is to illustratively provide a predetermined number of distinct sizes within a sufficiently necessary range of distinctly sized braces, whereby each individual customer is expected to fulfill his or her particular requirements through choosing one of these available sizes in the aforementioned sufficiently necessary range of distinctly sized braces.

BRIEF DESCRIPTION OF THE DRAWINGS

The invention will be best understood by those skilled in the art by reference to the accompanying drawings in which:

FIG. 6d shows a perspective view of part of a metal strip being embedded within the foot base portion and an exploded view of the associated metal plate incorporating the sole-raising spring shown in FIG. 6c dismantled in the constituent parts thereof and a cross sectional view of the assembly thereof.

FIG. 6e shows a perspective view of part of a metal strip being embedded within the foot base portion and an exploded view of the associated metal plate incorporating an endless screw member instead of the sole-raising spring shown in FIG. 6d.

FIG. 7a shows a metal strip of the foot base portion and an associated metal plate incorporating a sole-raising spring mechanism of the calf covering portion as shown in FIG. 6a being brought for connection and thereafter the same metal strip of the foot base portion being connected to its associate metal plate of the calf covering portion.

FIG. 7b shows a metal strip of the foot base portion connected to its associate metal plate of the calf covering portion incorporating the sole-raising spring as shown in the embodiment of FIG. 6b.

DESCRIPTION OF PREFERRED EMBODIMENTS OF THE INVENTION

The brace of the invention is adapted to provide sole raising assistance to patients exhibiting the condition known as drop foot and is offered ready to wear within ordinary shoes of any type. As shown in a first embodiment of the invention (FIG. 1 or FIG. 1a), the brace being provided as an ankle-foot orthosis (AFO) comprises a foot base portion 1 that includes a sole whereupon rests the foot of the user and a calf covering portion 2 that extends all along the shank bone of the calf thereof.

Figure 16:
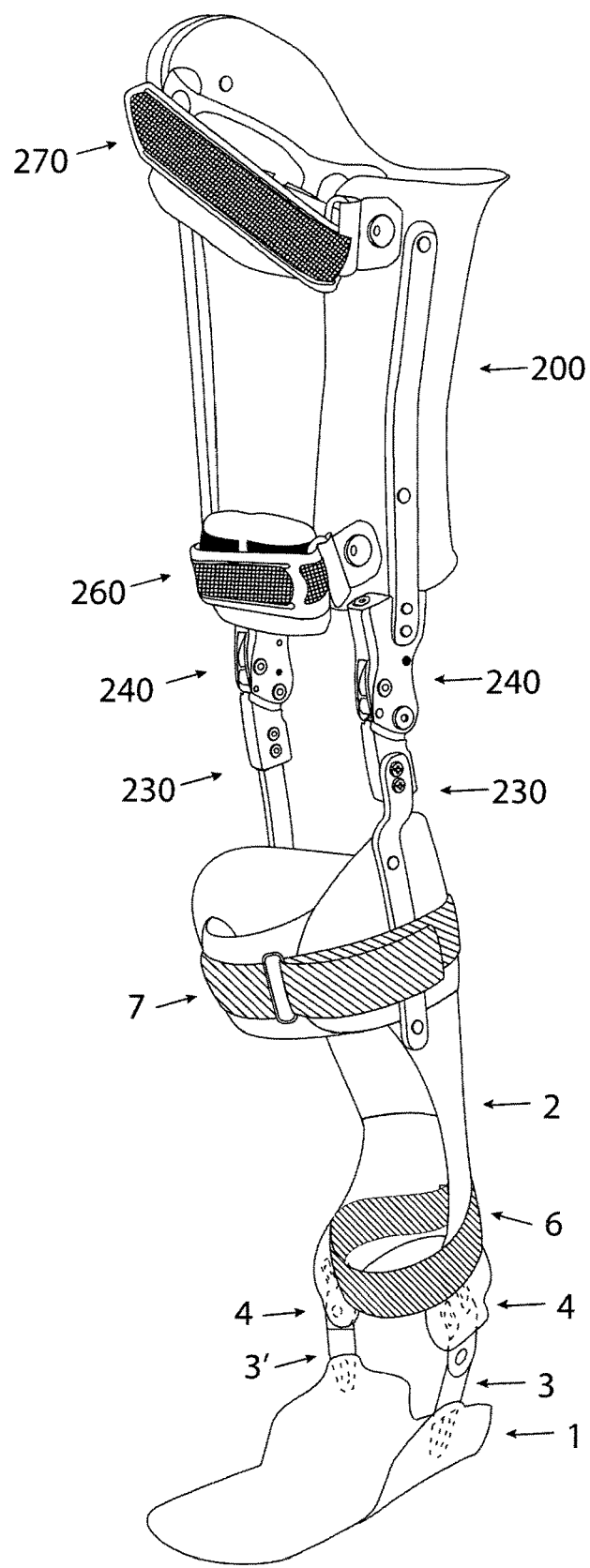
FIG. 16 shows a perspective view of an illustrative embodiment of the orthopedic brace of the invention including a femur covering portion.

Alternatively the brace might extend beyond the knee, along the thigh of the patient and operate as a knee-ankle-foot orthosis (KAFO) further comprising a femur covering portion 200 that extends upwardly the abovementioned calf covering portion 2. Such an illustrative form of a knee-ankle-foot orthosis (KAFO) is depicted in FIG. 16 and is connected to the calf covering portion 2 by means of bilaterally disposed metallic members 230 fixedly secured onto the sides of the calf covering portion 2 and pivotally connected to bilaterally disposed metallic plate members 240 fixedly connected at the sides of the femur covering portion 200, wherein a lower strap fastener profile 260 and an upper fastener profile 270 are adapted to securely fastening the aforementioned femur covering portion 200 along the femur of the user.

The foot base portion 1 of the brace comprises a sole portion 1c whereupon rests the foot of the user and a pair of upwardly extending flanges 1a, 1b at the rear of the sides thereof at the region of the talocrural articulation of an individual user, wherein the sole portion 1c and the upwardly extending flanges 1a, 1b constitute a single item being produced in a single appropriately formed mould. As shown in the exploded view of FIG. 2, the calf covering portion 2 on the other hand comprises an appropriately curved elongate member 2c that extends from the region proximate to the sole up to the region proximate to the knee of the user with a pair of bottom side flanges 2a, 2b and a pair of upper side flanges 2e, 2d.

In accordance with a preferred embodiment of the invention, a bilateral arrangement of hinge assembly mechanisms is employed to connect the aforementioned foot base portion 1 to the overlying calf covering portion 2, such hinge assembly mechanisms being adapted to effect a predetermined raising of the sole portion 1c so as to maintain the same at a predetermined appropriate angle with respect to the calf portion, thereby providing a nearly normal walking performance of the patient wearing the brace.

Figure 1:
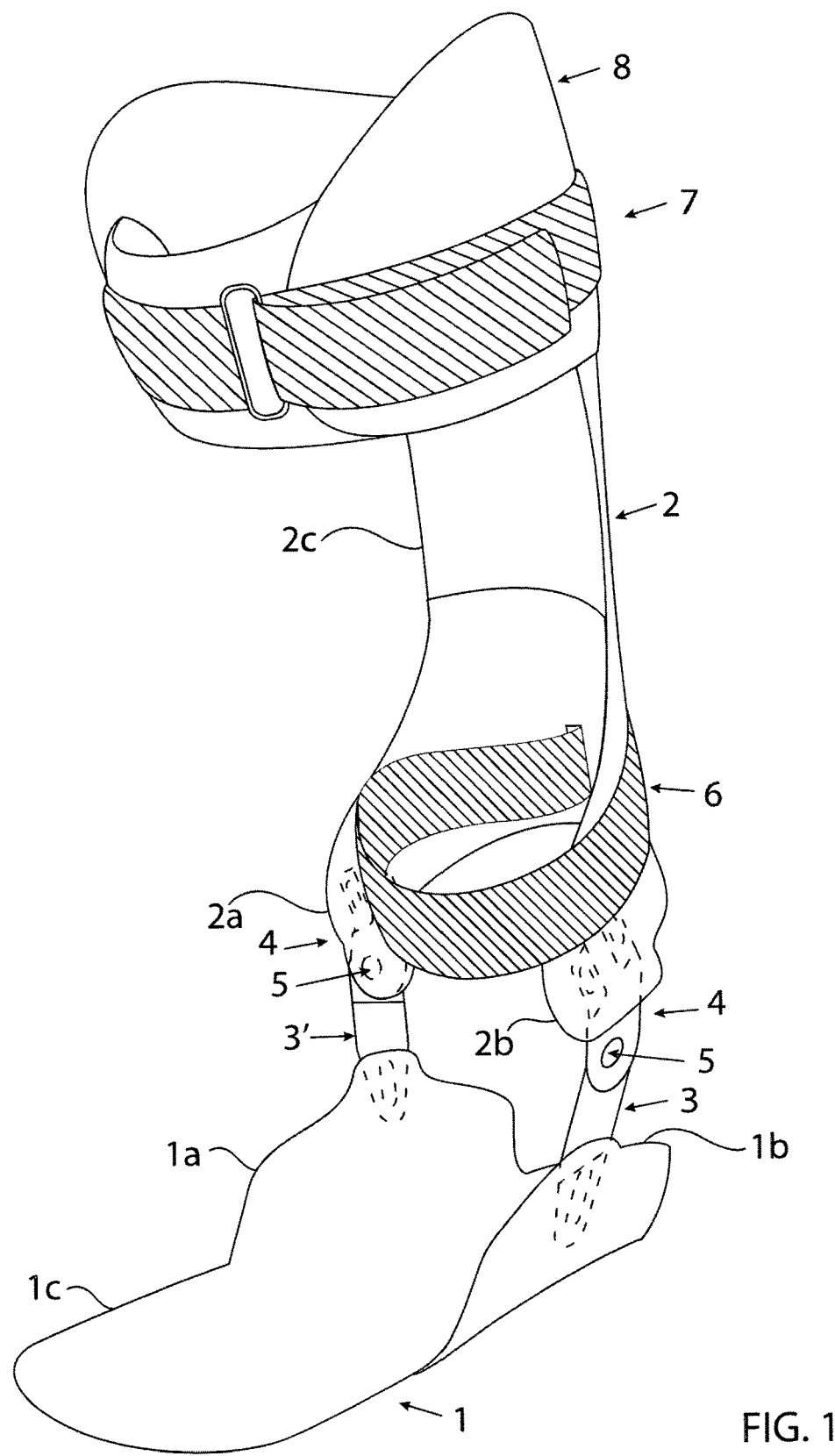
FIG. 1 shows a frontal perspective view of the orthopedic brace of the invention offered as an ankle-foot orthosis comprising a foot base portion and a calf covering portion pivotally connected to the foot base portion by means of a pair of sole-raising hinge assemblies, each sole-raising hinge assembly comprising a first metallic strip member fixedly embedded during a thermosetting process within an upwardly extending flange of the foot base portion and a second metallic plate member similarly fixedly embedded within an overlying flange of the calf covering portion, the latter being further provided with a pair of strap fastener profiles.
Figure 1A:
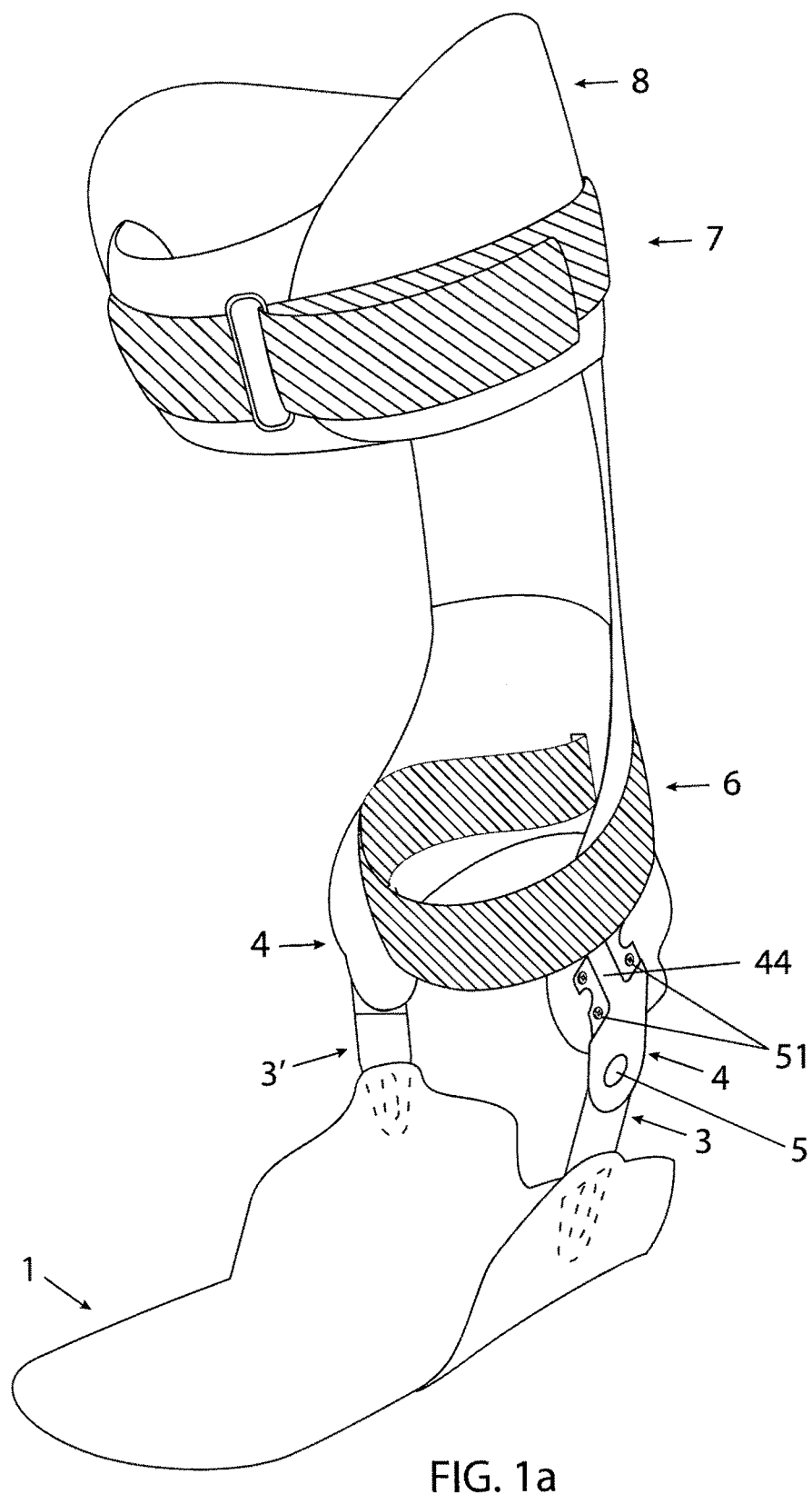
FIG. 1a shows a frontal perspective view of the orthopedic brace of the invention offered as an ankle-foot orthosis, wherein the first metallic strip member is fixedly embedded during a thermosetting process within an upwardly extending flange of the foot base portion, whilst the second metallic plate member is fixedly connected onto the overlying flange of the calf covering portion with an arrangement of bolts.
Figure 1B:
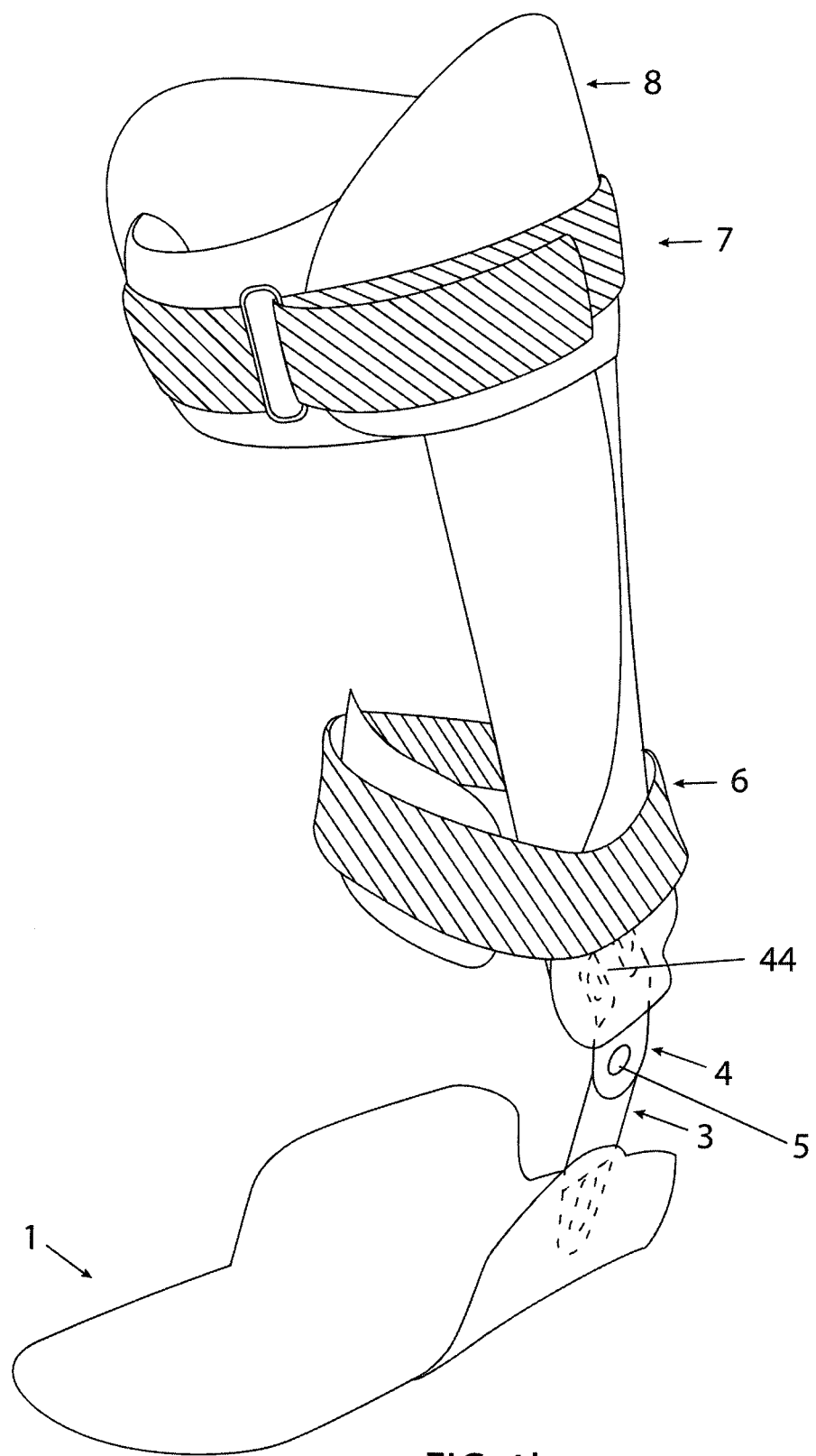
FIG. 1b shows the orthopaedic brace of the invention offered with an one-sided hinge assembly located in the inner part thereof.

In accordance with another embodiment of the invention, the orthopaedic brace might be offered with an one-sided hinge assembly located in the inner or the outer part thereof as illustrated in FIG. 1b, such embodiment being selected mainly for aesthetic reasons.

Figure 6A:
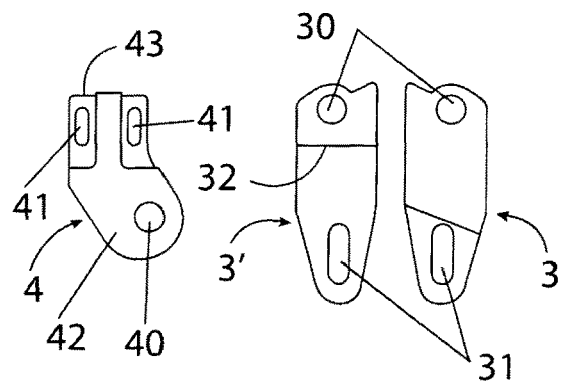
FIG. 6a shows a first illustrative embodiment of the constituent parts of the sole raising hinge assembly of the brace of the invention, each such assembly comprising a pair of metal strips being embedded within the lateral flanges of the foot base portion and a pair of associated metal plates incorporating sole-raising spring mechanisms being embedded within the lateral bottom end flanges of the calf covering portion.

The abovementioned hinge assembly mechanism comprises a first metallic strip member 3, 3' appropriately connected at each one of the upwardly extending flanges 1a, 1b of the sole portion 1c and a second metallic plate member 4 that is being connected at each one of the abovementioned pair of bottom side flanges 2a, 2b of the calf covering portion 2, said side flanges 2a, 2b being appropriately located above said upwardly extending flanges 1a, 1b of the foot base portion 1 with a scope of pivotally connecting the calf covering portion to the foot base portion by means of the pivotal connection of the aforementioned first metallic strip member 3 and 3' to the overlying second metallic plate member 4 of each one of the bilaterally provided hinge assembly mechanisms. A pair of items of the abovementioned second metallic plate member 4 are used in the two side flanges 2a, 2b of the calf covering portion, whilst a pair of distinct items of the first metallic strip member 3, 3' are employed in association with the upwardly raised side flanges 1b, 1a of the foot base portion 1 respectively to appropriately adapt to the configuration of the corresponding malleolus medialis and malleolus lateralis. Thus, as shown in FIG. 6a or FIG. 6c, whilst the first metallic strip member 3 is a planar strip, the first metallic strip member 3' is not and it is instead bent outwardly at an intermediate bend level 32 upwardly lateral flange 1a of the foot base portion thereby appropriately providing for the protruding configuration of the ankle.

The pivotal connection of the first metallic strip member 3, 3' to the second metallic plate member 4 of each hinge assembly and accordingly of the foot base portion 1 with the calf covering portion 2 is being effected by means of bolt connector means 5 that passes though a pair of coincidentally aligned holes, i.e. a hole 30 provided at the free end of the first metallic strip member 3, 3' extending beyond the flanges 1b, 1a of the foot base portion 1 and a hole 40 provided at the free end of the second metallic plate member 4 extending beyond the flanges 2a, 2b of the calf covering portion 2.

With a scope of providing a drop foot correcting brace product at low cost, however with optimal performance, long service life and high aesthetics, and most importantly providing such drop foot correcting brace product ready to wear, the invention proposes manufacturing the constituent parts of the foot base portion 1 and calf covering portion 2 in an industrial thermosetting process, wherein the foot base portion is made using suitable moulds within which appropriate plastic raw material is being injected. The calf covering portion is manufactured with an analogous industrial thermosetting process with injection molding within correspondingly appropriate calf covering portion producing molds. A characteristic feature of such injection molding thermosetting process is that the first metallic strip member 3, 3' is being embedded within the corresponding lateral flanges 1b, 1a of the sole member 1c of the foot base portion and is thereby fixedly held therein, such process eliminating the need of the employment of bolts for the connection of such first metallic strip member 3, 3' onto the lateral flanges 1b, 1a. For implementing the abovementioned process of manufacturing a foot base portion 1 with a pair of first metallic strip members 3, 3' of the hinge assembly mechanism embedded within the lateral flanges 1b, 1a thereof, a bottom portion of the first metallic strip member 3, 3' that is adapted to be embedded within the lateral flanges 1b, 1a of the sole member 1c of the foot base portion is provided with suitably configured apertures, e.g. an elongate elliptical aperture 31 that is being filled with the plastic raw material and is thereby fixedly held within the lateral flanges 1a, 1b of the sole member 1c as the thermosetting process is being concluded. Different configurations of the aperture 31 are also possible, e.g. one or more square, rectangular, polygonal, circular or other linear and/or curved apertures or any combination of such aperture configurations as long as they suitably fulfill the requirement of being filled with plastic material during the injection thermosetting process of manufacturing the foot base portion 1 and effecting embedding of the first metallic strip member 3, 3' within the lateral flanges 1b and 1a respectively.

Figure 6B:
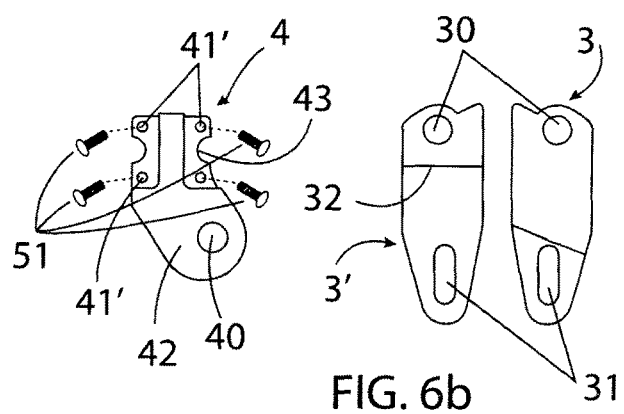
FIG. 6b shows a second illustrative embodiment of the constituent parts of the sole raising hinge assembly of the brace of the invention, each such assembly comprising a pair of metal strips being embedded within the lateral flanges of the foot base portion and a pair of associated metal plates incorporating sole-raising spring mechanisms being fixedly bolted into appropriate positions onto the lateral bottom end flanges of the calf covering portion.
Figure 6C:
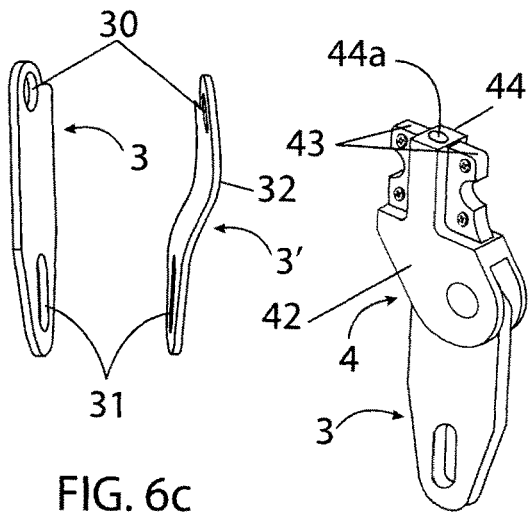
FIG. 6c shows a perspective view of the pair of metal strips being embedded within the lateral flanges of the foot base portion of FIGS. 6a, 6b together with an assembled associated metal plate incorporating the sole-raising spring mechanism as shown in FIG. 6b.

The second metallic plate member 4 of the hinge assembly of the invention, as illustratively shown in FIGS. 6b, 6c and 6d, comprises a pair of parallel plates 42 which extend downwardly beyond the flanges 2a, 2b of the calf covering portion 2, wherein these parallel plates 42 are provided with coaxially oriented holes 40 and are adapted to receive the upper portion of the first metallic strip members 3, 3' within the gap being provided in between them in a way such that the hole 30 being provided at the upper portion of each one of the first metallic strip members 3, 3' is brought in alignment with the aforementioned coaxially oriented holes 40 of the parallel plates 42, whereby bolt connecting means 5 passes through coincident holes 30 and 40 and is secured by nut means 5a (FIG. 6d) thereby effecting pivotal connection of the first metallic strip member 3, 3' with the second metallic plate member 4 of the hinge assembly of the invention, the pivotal axis being defined by the aforementioned bolt connecting means 5.

The upper portion of the second metallic plate member 4 of the hinge assembly is provided with a rectilinear member 44 with an axial tubular housing 44a adapted to receive an elongate compression spring 45 that seats onto a seat member 46 first introduced into the tubular housing 44a and is delimited by a bolt member 47 that serves as a top cover of the tubular housing 44a, such bolt member 47 being variably screwed within the tubular housing so as to effect a variable tension of the aforementioned elongate compression spring 45. A pair of identical side flange extensions 43 is provided on either side of the above rectilinear member 44 of the metallic plate member 4, such side flange extensions being appropriately configured for effecting connection of the metallic plate member 4 onto the flanges 2a, 2b of the calf covering portion 2 of the brace of the invention.

In accordance with a first preferred embodiment of the invention, the abovementioned side flange extensions 43 of the second metallic plate member 4 of the hinge assembly might be provided with suitably arranged holes 41' adapted to receive bolts 51 for fixedly securing metallic plate member 4 onto the flanges 2a, 2b of the calf covering portion 2 (FIGS. 6b, 6d). FIG. 1a shows a frontal perspective view of the orthopedic brace of the invention offered as an ankle-foot orthosis, wherein the first metallic strip members 3, 3' are fixedly embedded during a thermosetting process within upwardly extending flanges 1b, 1a of the foot base portion 1, whilst the corresponding second metallic plate members 4 are fixedly connected onto the overlying flanges 2a, 2b of the calf covering portion 2 with an arrangement of bolts 51.

Alternatively, in accordance with a second preferred embodiment of the invention, the abovementioned side flange extensions 43 of the second metallic plate member 4 of the hinge assembly might be provided with suitably configured apertures, e.g. elongate elliptical apertures 41 being filled with the plastic raw material during the thermosetting process of industrial production of the overall calf covering portion 2 and is thereby fixedly held within the aforementioned flanges 2a, 2b of the calf covering portion 2 as the thermosetting process of industrial production of calf covering portions 2 is being concluded (FIGS. 6a, 7a). FIG. 1 shows a frontal perspective view of the orthopedic brace of the invention offered as an ankle-foot orthosis, wherein each sole-raising hinge assembly comprises a first metallic strip member fixedly embedded during a thermosetting process within an upwardly extending flange of the foot base portion and a second metallic plate member similarly fixedly embedded within an overlying flange of the calf covering portion.

The thermosetting industrial process of manufacturing the brace of the invention in combination with embedding one and preferably both members of the hinge assemblies within the foot base portion 1 and the calf covering portion 2 thereof as described hereinabove provides the capacity of offering the orthopedic brace as a ready to wear product. In this respect the human anatomy has been carefully considered to provide distinct ready to wear sizes that might be comfortably worn by users with varying anatomical characteristics.

Figure 8A:
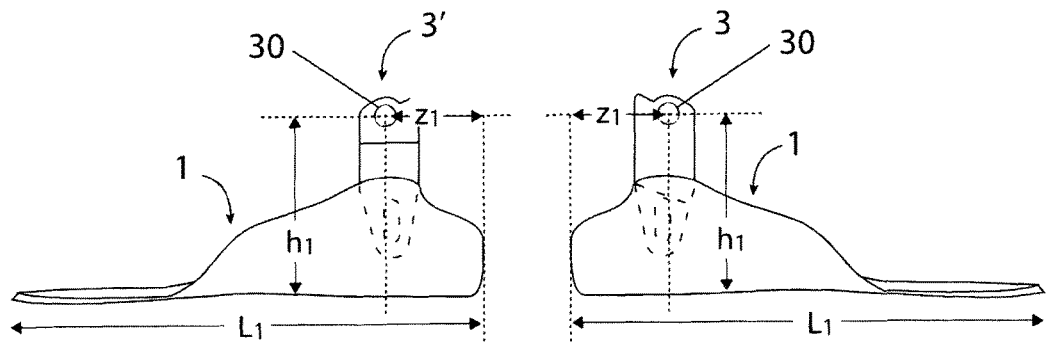
FIG. 8a shows a side view of the foot base portion of the orthopedic brace of the invention and in particular of one and of the other lateral flanges thereof with the metal strips of the sole raising hinge assemblies being embedded therein.
Figure 8B:
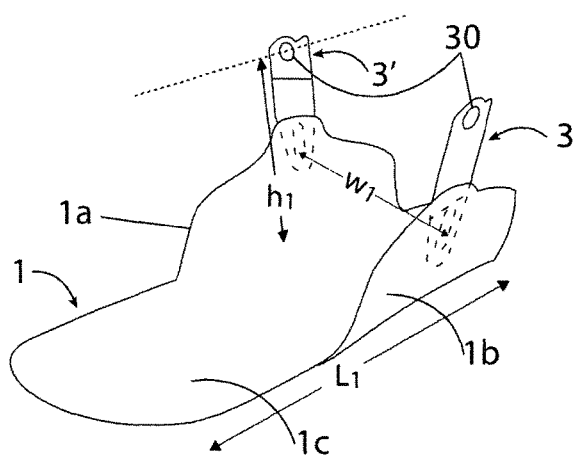
FIG. 8b shows a perspective view of a foot base portion with the metal strips of the sole raising hinge assemblies being embedded within the lateral flanges thereof.

As shown in FIGS. 8a and 8b, the foot base portion 1 of the orthopedic brace of the invention with the metallic strip members 3, 3' embedded in the lateral flanges 1b and 1a thereof respectively is characterized by the following variable parameters:
- a length $L_1$ as defined by the distance of the rear to the frontal end of the sole base portion 1c;
- a height $h_1$ as defined by the distance of the sole base portion 1c from the hole 30 being provided at the upper portion of each one of the first metallic strip members 3, 3';
- a length $Z_1$ as defined by the distance of the hole 30 being provided at the upper portion of each one of the first metallic strip members 3, 3' from the rear end of the sole base portion 1c, and
- a width $W_1$ as defined by the distance between the upwardly oriented lateral flanges 1a, 1b of the foot base portion 1.

Figure 8C:
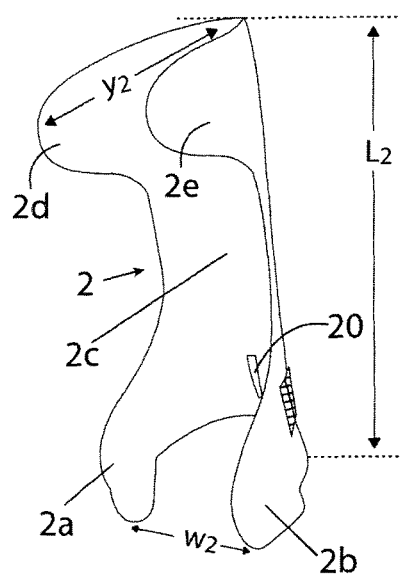
FIG. 8c shows a perspective view of the calf covering portion of the orthopedic brace of the invention.
Figure 9A:
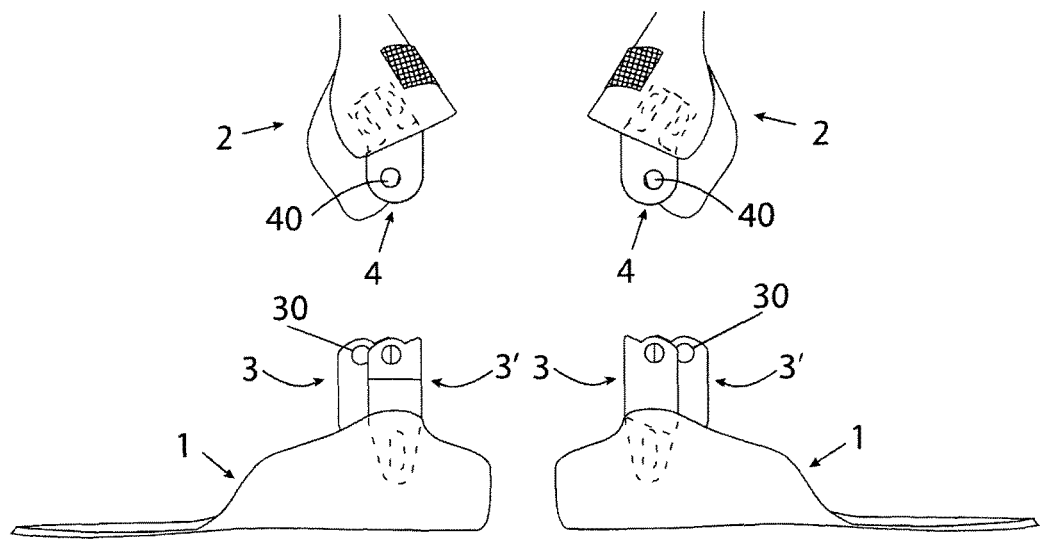
FIG. 9a shows a calf covering portion of the orthopedic brace of the invention being brought in a mating orientation above a right and a left foot base portion respectively.
Figure 9B:
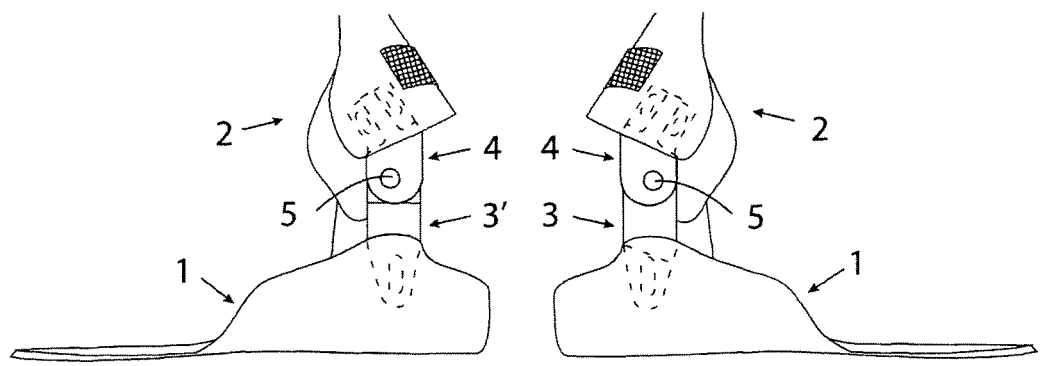
FIG. 9b shows the calf covering portions of the orthopedic brace of the invention depicted in FIG. 9a connected to the right and left foot base portion respectively.

Further, as shown in FIG. 8c, the calf covering portion of the orthopedic brace of the invention is characterized by the following variable parameters:
- a length $L_2$ as defined by the distance of the bottom to the top of the calf covering portion 2 measured in the longitudinal direction of the leg of the user;
- a depth $Y_2$ as defined by the distance of the rear of the calf covering 2 from the frontal ends of the pair of upper side flanges 2e, 2d thereof, and
- a width $W_2$ as defined by the distance between the forwardly oriented lateral flanges 2a, 2b of the calf covering portion 2.

With a scope of providing a collection of sizes of the orthopedic brace of the invention suitable for the vast majority of users with varying anatomical characteristics, the industrially produced orthopedic brace sizes are provided with progressively and proportionally increasing dimensions ($L_1$, $Z_1$, $W_1$) for the foot base portion 1 and correspondingly progressively and proportionally increasing dimensions ($L_2$, $Y_2$, $W_2$) for the calf covering portion 2. In as far as the height parameter $h_1$ is concerned, this can remain constant in the various sizes or it may also be progressively and proportionally varied. By way of example, the aforementioned collection of sizes of the orthopedic brace of the invention comprises six distinct sizes that constitute a sufficiently necessary range of distinctly sized braces that includes an extra-small (XS), a small (S), a medium (M), a large (L), an extra-large (XL) and an extra-extra-large (XXL) size, whereby each individual customer is expected to fulfill his or her particular requirements through choosing one of these available sizes in the aforementioned sufficiently necessary range of distinctly sized braces. In another example, it is considered sufficient to provide two distinct sizes for two broad categories of users with small to medium anatomical characteristics on the one hand and with medium to large anatomical characteristics on the other hand.

It is hereby noted that in accordance with an alternative embodiment of the invention, as shown in FIG. 6e, the aforementioned compression springs 45 of the second metallic plate member 4 of the hinge assembly are replaced with endless screw members 48, which are inserted within the tubular housing 44a and are advanced downwardly as they are being screwed within the tubular housing 44a thereby exerting pressure upon an upper edges 38 of the metallic strip members 3, 3' of the hinge assembly, which are embedded within the lateral flanges of the foot base portion 1. This embodiment of the brace of the invention can be employed with a scope of providing assistance to persons suffering from ippopodia (pes equinus), that is a permanent deformation of the foot in plantar flexion, especially used during night resting.

Figure 2:
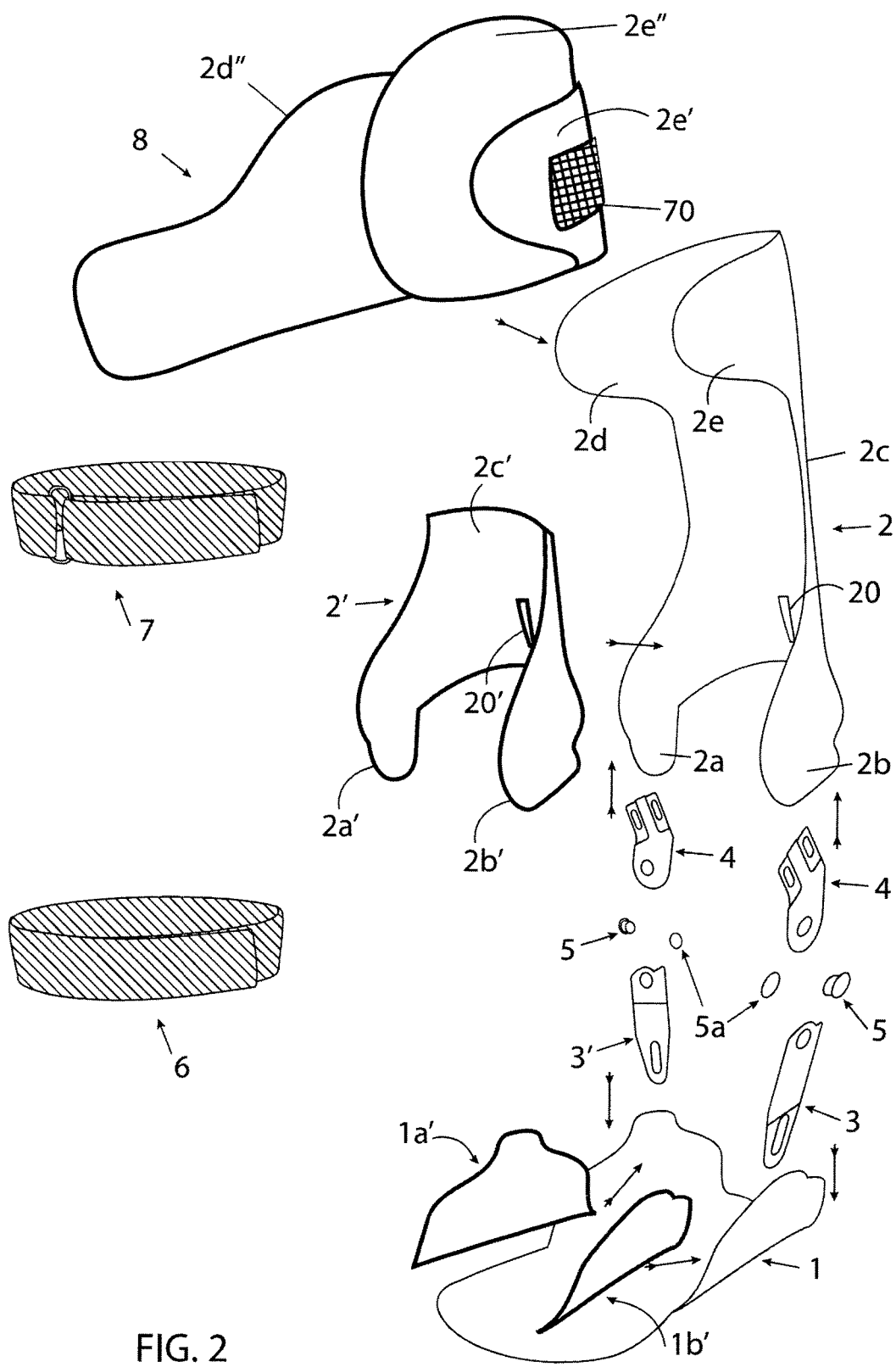
FIG. 2 shows a perspective view of the orthopedic brace of the invention shown in FIG. 1 dismantled in the constituent parts thereof.
Figure 3:
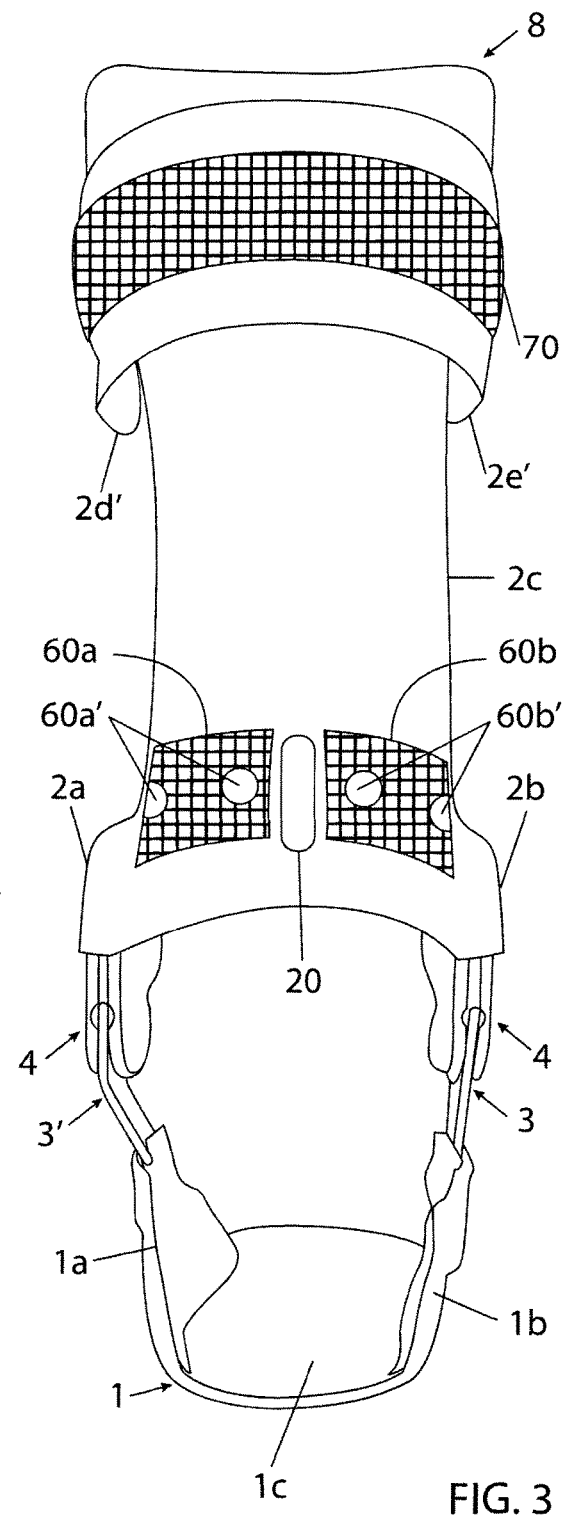
FIG. 3 shows a rear perspective view of the orthopedic brace of the invention shown in FIG. 1.

As illustratively shown in the exploded view of the brace of the invention in FIG. 2, appropriately formed comfort enhancing textile patches might be employed to cover parts of the foot base portion 1 and/or the calf covering portion 2 of the brace of the invention. By way of example, textile patches 1a', 1b' might be provided for covering the upwardly oriented lateral flanges 1a, 1b of the foot base portion 1 respectively, whilst appropriately configured patches might be employed to cover parts or the entire interior of the calf covering portion 2 as well. In relation to the embodiment depicted in FIG. 2, an upper textile patch 8 is employed to be fitted so as to cover the upper part of the calf covering portion 2 and another lower textile patch 2' is employed to cover the interior lower part thereof. The upper textile patch 8 comprises extensions 2d', 2e' covering the upper lateral flanges 2d, 2e respectively and extensions 2d", 2e" extending beyond the lateral flanges 2d, 2e respectively. The lower textile patch 2' comprises extensions 2a', 2W covering the lower lateral flanges 2a, 2b respectively and a portion 2c' that partly covers the elongate interior 2c of the calf covering portion. The lower textile patch 2' is further shown to comprise an elongate aperture 20' that coincides with a characteristic elongate vertically oriented aperture 20 of the calf covering portion 2 when the lower textile patch 2' is applied onto the interior of the calf covering portion 2 of the brace of the invention. As shown in FIG. 3, the exterior of the calf covering portion 2 is provided with a hooked strip surface 70 proximately the top thereof and a pair of hooked strip surfaces 60a, 60b located on either side of central elongate aperture 20 proximately the bottom of the calf covering portion 2, such hooked strip surfaces 60a, 60b being appropriately glued onto the exterior surface of the calf covering portion 2 or being riveted thereupon by means of rivets 60a', 60b' respectively.

Figure 15:
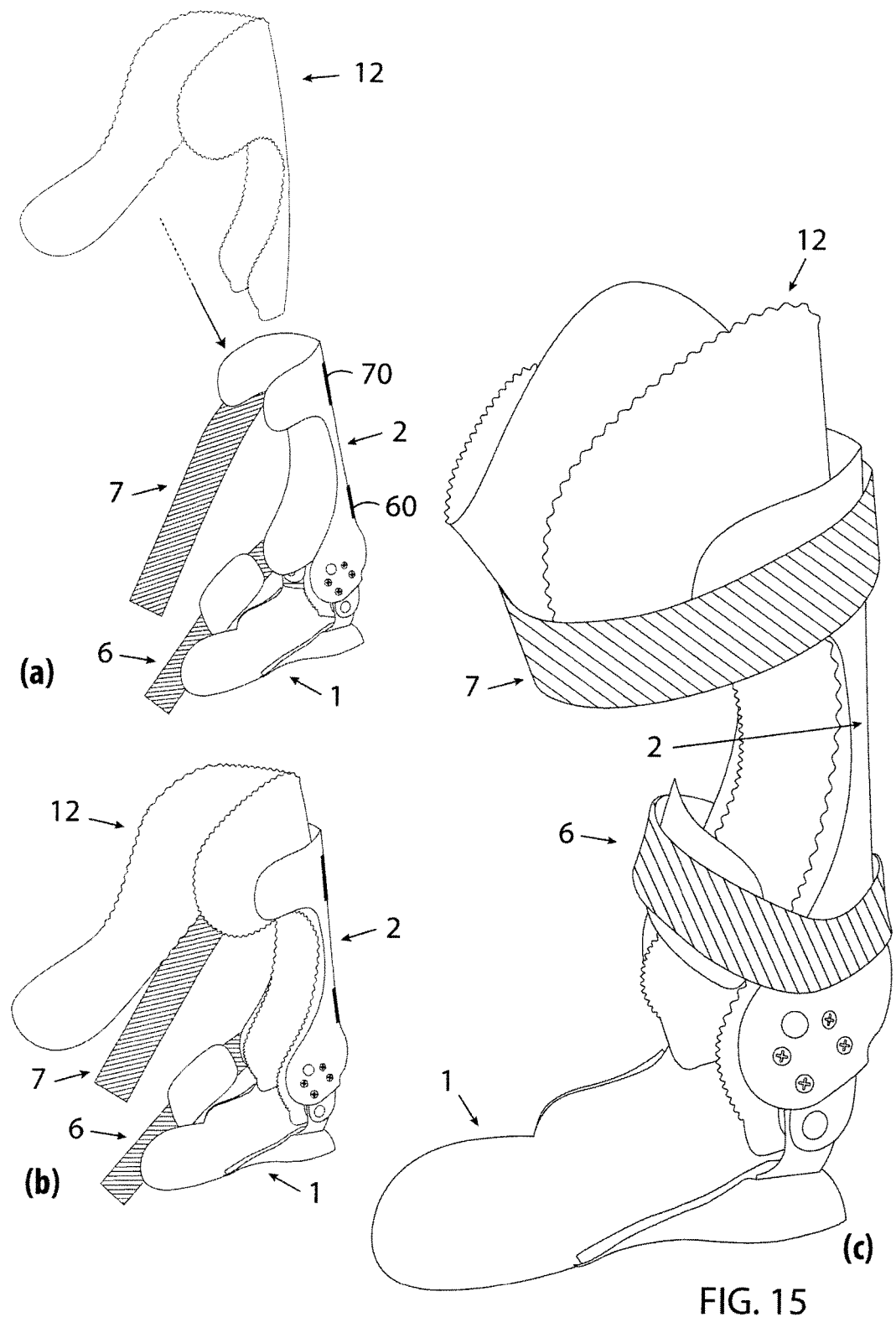
FIG. 15 shows an alternative embodiment of the brace of the invention with a single textile patch covering of the interior surface of the calf covering portion.

In accordance with an alternative embodiment of the invention illustratively depicted in FIG. 15, a single textile patch 12 is employed to cover the entire interior of the calf covering portion 2. In this case the hooked strip surface 70 is provided at the rear of the upper part of the calf covering portion 2 instead of being provided at the rear of the upper textile patch 8 as is the case with the embodiment depicted in FIG. 2. FIG. 15 shows successively in pictures (a), (b), (c) the single textile patch 12 outside the brace (FIG. 15a), the single textile patch 12 fitted onto the interior of the calf covering portion 2 (FIG. 15b) and the orthopedic brace with strap fastener profiles 6 and 7 appropriately fastened (FIG. 15c).

An upper strap fastener profile 7 and a lower strap fastener profile 6 are provided in combination with a scope of providing a firm adjustment of the brace onto the leg of each individual user, such lower and upper strap fastener profiles 6 and 7 being correspondingly used in association with the abovementioned hooked strip surfaces 60a, 60b proximately the bottom of the exterior surface and hooked strip surface 70 proximately the top of the exterior surface of the calf covering portion 2.

Figure 4:
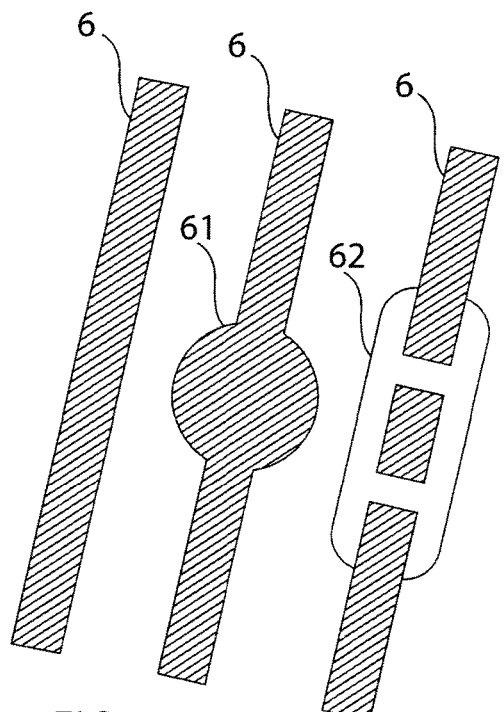
FIG. 4 shows illustrative forms of the lower and of the upper strap fastener profile being employed in the orthopedic brace of the invention shown in FIG. 1.

FIG. 4 shows alternative illustrative forms of the lower strap fastener profile 6 being employed in the orthopedic brace of the invention, wherein strap fastener profile 6 may be a linear strap having a length such as to surround the calf covering portion 2 proximately to the bottom thereof with a surface 6a that is depicted in the drawings with parallel line shading and a surface 6b being depicted with a shading of an array of squares, both these surfaces 6a, 6b of the strap fattener profile 6 having a loop texture such as to be firmly adhered when abutting onto the aforementioned hooked strip surfaces 60a, 60b proximately the bottom of the exterior of the calf covering portion 2. Furthermore strap fastener profile 6 might comprise a central enlarged portion, such as the round portion 61 or it might be employed in association with an independent strip portion 62 provided with slots allowing passage of the strap fastener profile therein.

Figure 10:
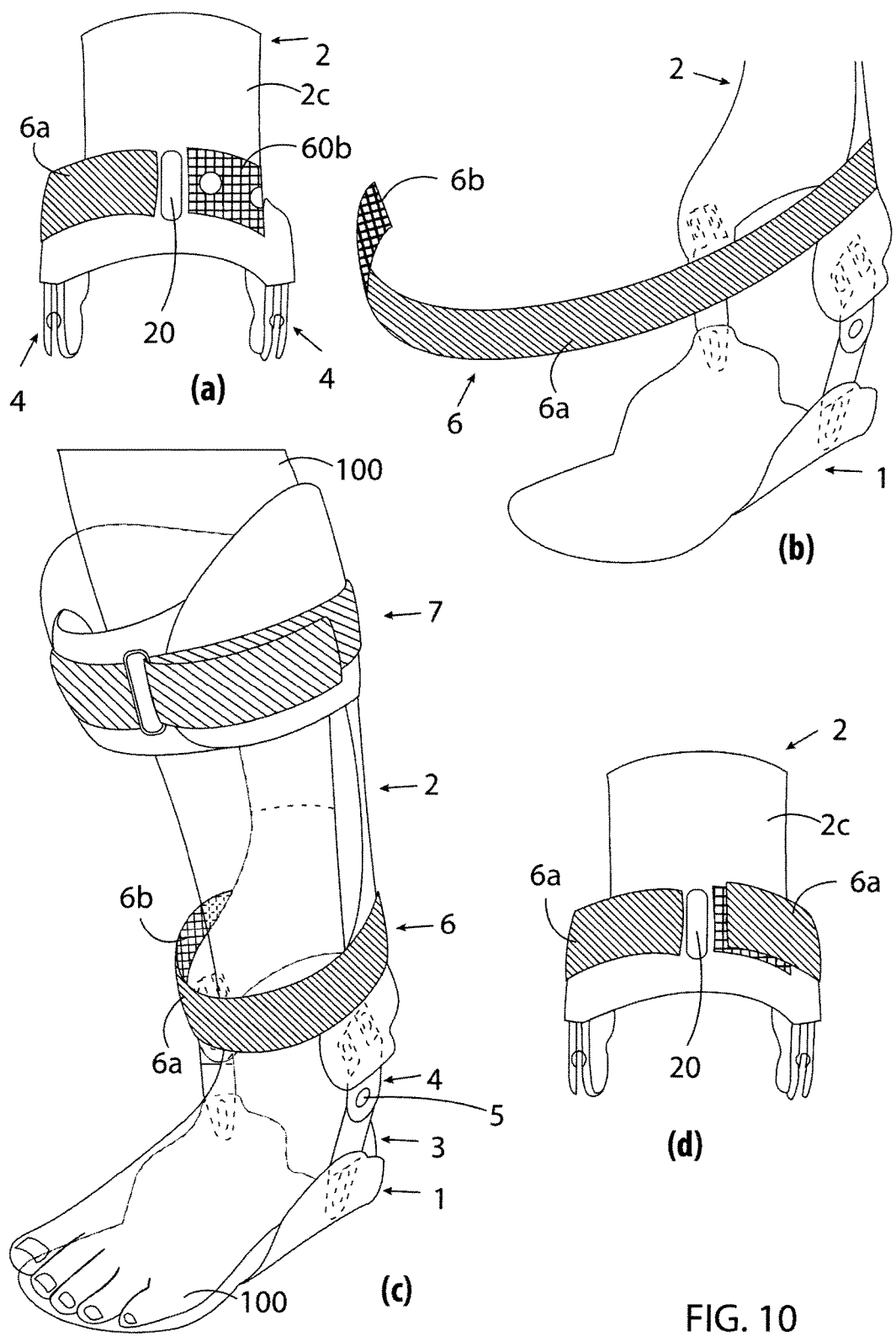
FIG. 10 shows sequential steps of positioning and fastening the lower strap fastener profile of the orthopedic brace of the invention.
Figure 11:
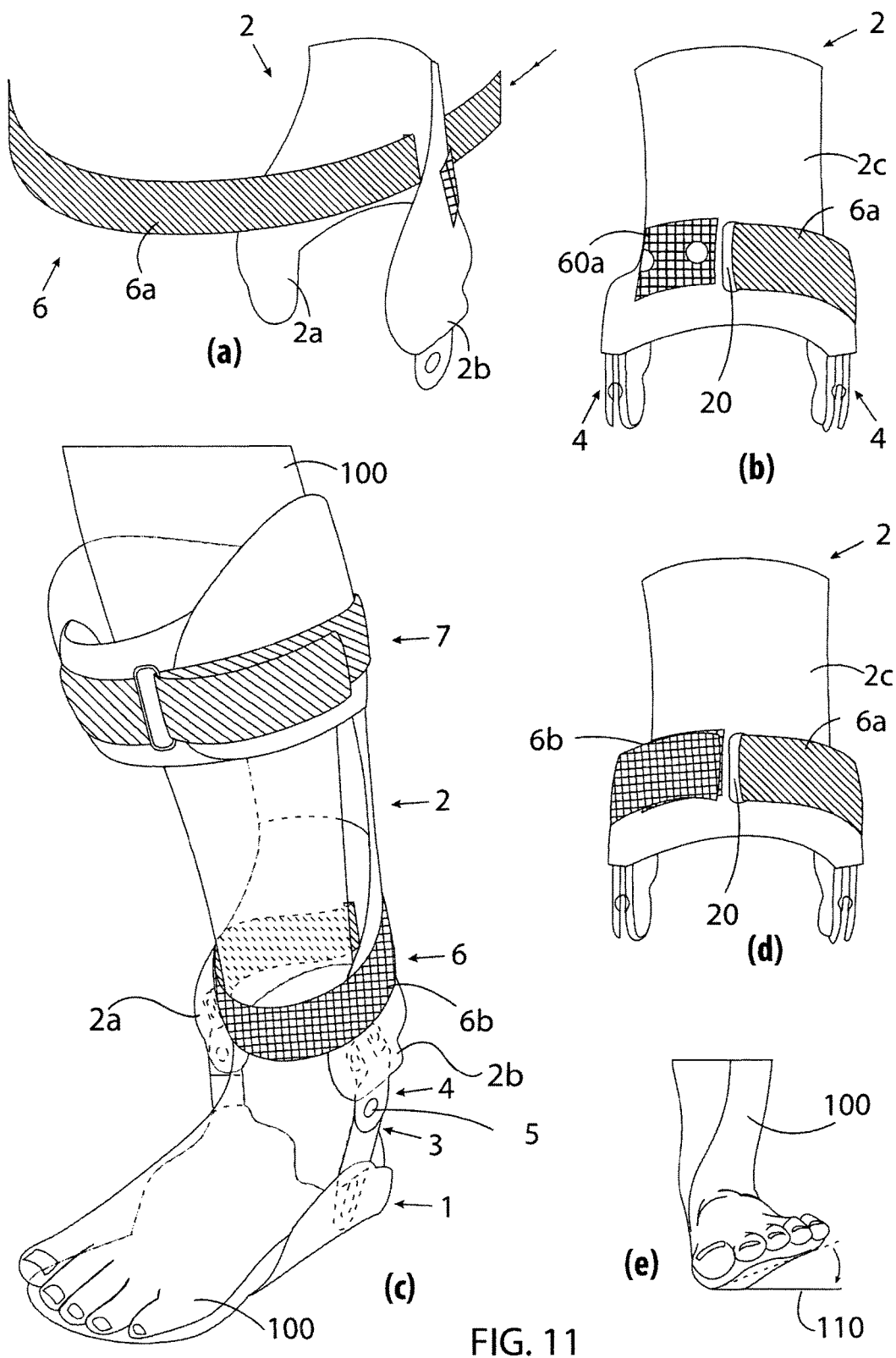
FIG. 11 shows sequential steps of positioning and fastening the lower strap fastener profile of the orthopedic brace of the invention when such lower strap fastener profile is adapted to provide correction of structural varus type misalignment of the foot of the user.
Figure 12:
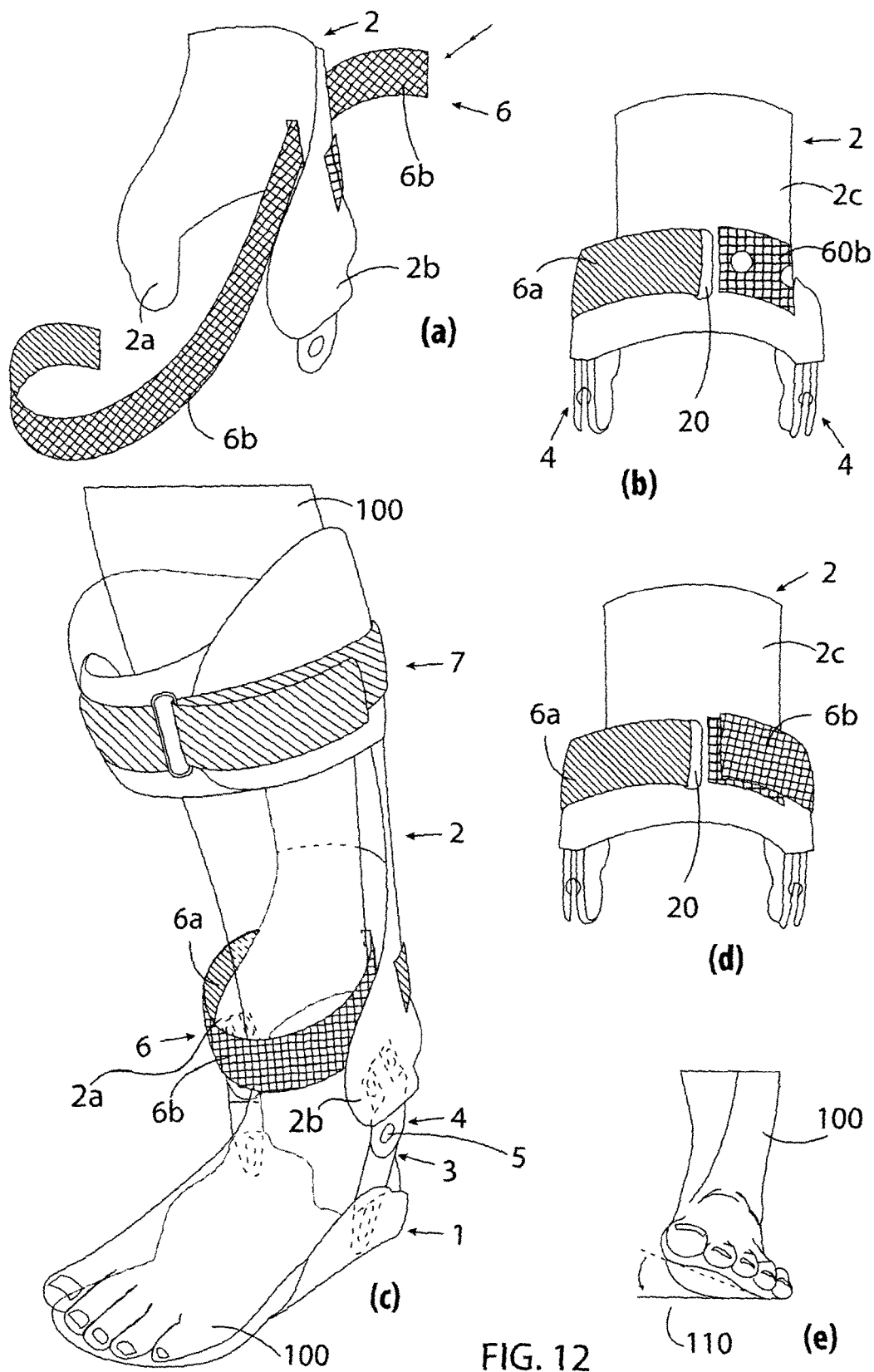
FIG. 12 shows sequential steps of positioning and fastening the lower strap fastener profile of the orthopedic brace of the invention when such lower strap fastener profile is adapted to provide correction of structural valgus type misalignment of the foot of the user.

FIGS. 10, 11 and 12 show sequential steps of a method of positioning and fastening the lower strap fastener profile 6 of the orthopedic brace of the invention in the distinct cases of using the strap fastener profile 6 as a simple means of fastening the calf covering portion 2 onto the leg of the user (FIG. 10) and as a means of fastening with the additional function of providing correction of structural misalignment of the foot of the user of either the varus type (FIG. 11) or the valgus type (FIG. 12).

In particular as shown in sequential pictures (a)-(d) of FIG. 10 in the embodiment of the strap being employed as a simple fastening means, the sequential steps of positioning and fastening the lower strap fastener profile 6 onto the calf covering portion 2 have as follows:

A first step comprises attachment of one end of the surface 6b with the shading of an array of squares of a first end of the strap fastener profile 6 onto either one of the hooked strip surfaces 60a, 60b proximately the bottom of the exterior of the calf covering portion 2, and in particular onto surface 60a in the example depicted in FIG. 10a.

A second step comprises surrounding the calf covering portion 2 with the leg 100 of the user therein by turning the strap fastener profile 6 in a clockwise direction (FIG. 10b); it is noted that if the surface 6b of the strap fastener profile 6 had during the first step hereinabove been alternatively attached onto the hooked strip surface 60b it would have to be turned in an anticlockwise direction in this second step. Thus alternative attachment onto either surface 60a or surface 60b would provide comfortable use for right-handed and left-handed users.

A third step comprises firmly holding the leg 100 within the calf covering portion 2 by pulling the strap fastener profile 6 and bringing the free end thereof at the rear of the calf covering portion 2 wherein this free end is being attached onto hooked strip surface 60b (FIGS. 10c, 10d).

In accordance with the alternative embodiment of the invention as shown in the sequential pictures (a)-(d) of FIG. 11, the lower strap fastener profile 6 is employed in a mode such as to offer correction of the valgus abnormality that specifically refers to a position of the sole or of any part of the foot, wherein the sole is turned outward or is being everted, that is away from the body midline to an abnormal degree, such condition being illustrated in the detail of FIG. 11e. In this embodiment, the sequential steps of positioning and fastening the lower strap fastener profile 6 onto the calf covering portion 2 have as follows:

A first step comprises passage of a first end of the strap fastener profile 6 through central aperture 20 of the calf covering portion 2, the total length passed at the rear of the calf covering portion 2 corresponding to the necessary length for attachment onto the hooked strip surface 60b of the calf covering portion 2 (FIG. 11a).

A second step comprises attachment of the surface 6b with the shading of an array of squares of the abovementioned length of the strap fastener profile 6 that has passed through central aperture 20 onto the hooked strip surface 60b proximately the bottom of the exterior of the calf covering portion 2 (FIG. 11b).

A third step comprises bringing the strap fastener profile 6 in abutment with the inner surface of the calf covering portion 2 and dragging the free end of the strap fastener profile 6 in an anticlockwise direction thereby surrounding the leg 100 of the user without surrounding the exterior surface of the calf covering portion with the flange 2a, pulling the same and surrounding the exterior surface of the calf covering portion 2 with the flange 2b to bring the second end of the strap fastener profile 6 at the rear of the calf covering portion 2 (FIG. 11c);

A fourth step comprises firmly holding the leg 100 within the calf covering portion 2 by pulling the strap, thereby effecting correction of the valgus type misalignment depicted in FIG. 11e and bringing the second end of the strap fastener profile 6 at the rear of the calf covering portion wherein this second end is being attached onto hooked strip surface 60a (FIG. 11d).

In accordance with the alternative embodiment of the invention as shown in the sequential pictures (a)-(d) of FIG. 12, the lower strap fastener profile 6 is employed in a mode such as to offer correction of the varus type abnormality that specifically refers to a position of the sole or of any part of the foot, wherein the sole is turned inward or is inverted, that is towards the body midline to an abnormal degree, such condition being illustrated in the detail of FIG. 12e. In this embodiment, the sequential steps of positioning and fastening the lower strap fastener profile 6 onto the calf covering portion 2 have as follows:

A first step comprises passage of a first end of the strap fastener profile 6 through central aperture 20 of the calf covering portion, the total length passed corresponding to the necessary length for attachment onto the hooked strip surface 60a of the calf covering portion (FIG. 12a).

A second step comprises attachment of the surface 6*b* with the shading of an array of squares of the abovementioned length of the strap fastener profile 6 that has passed through central aperture 20 onto the hooked strip surface 60*a* proximately the bottom of the exterior of the calf covering portion 2 (FIG. 12*b*).

A third step comprises bringing the strap fastener profile 6 in abutment with the inner surface of the calf covering portion 2 and pulling the free end of the strap fastener profile 6 in a clockwise direction thereby surrounding the leg 100 of the user without surrounding the exterior of the calf covering portion with the flange 2*b*, pulling the same and surrounding the exterior of the calf covering portion 2 with the flange 2*a* to bring the second end of the strap fastener profile 6 at the rear of the calf covering portion 2 (FIG. 12*c*);

A fourth step comprises firmly holding the leg within the calf covering portion 2 by pulling the strap, thereby effecting correction of the varus type misalignment depicted in FIG. 11*e* and bringing the second end of the strap fastener profile 6 at the rear of the calf covering portion wherein this second end is being attached onto hooked strip surface 60*b* (FIG. 12*d*).

It is therefore made clear from the description provided hereinabove that a process of distinctly fastening the strap fastener profile 6 is disclosed in the present invention, whereby the strap fastener profile 6 is alternatively being used as a simple means of fastening the calf covering portion 2 onto the leg of the user (FIG. 10) or as a means of fastening with the additional function of providing correction of structural misalignment of the foot of the user of either the varus type (FIG. 11) or the valgus type (FIG. 12).

Figure 5:
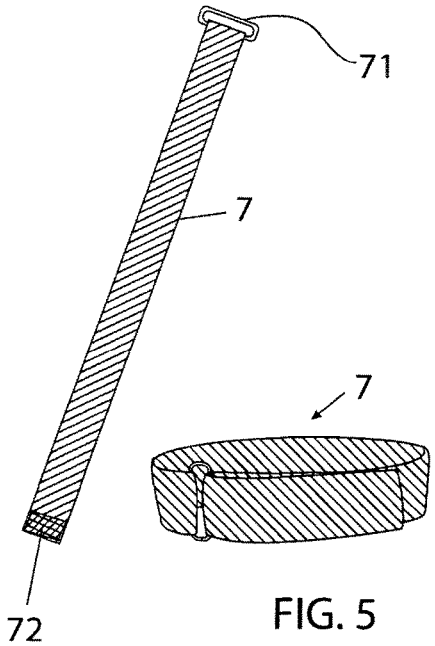
FIG. 5 shows the upper strap fastener profile being employed in the orthopedic brace of the invention shown in FIG. 1 in a straight extended form prior to use and in a coiled form as actually used.

A further strap fastener profile 7 is further being used as a means of fastening the calf covering portion 2 onto the leg of the user, such strap fastener profile being employed in securely mounting the orthopedic brace of the invention onto the leg of the user at the upper part of the calf covering portion 2. As shown in FIG. 5, this upper strap fastener profile 7 is a linear strap having a length such as to surround the calf covering portion 2 proximately to the top thereof. In accordance with a preferred embodiment of the invention both sides of the strap 7 have a loop texture, such that they may not adhere onto a textile surface of the cloth worn by the user and such that they might adhere and be fixedly mounted when abutting onto the hooked strip surface 70 that extends around the rear exterior surface of either the calf covering portion 2 or onto a similar hooked strip surface provided onto the upper textile patch 8 that is being fitted onto the upper portion of the calf covering portion 2.

In accordance with a preferred embodiment of the invention, one end of the strap fastener profile 7 is provided with a buckle 71 and the other free end 72 thereof is provided with an end hooked surface portion 72*a* at one side of the strap fastener profile 7, such hooked surface portion being depicted in the drawings with the shading of an array of squares, such end hooked surface portion 72*a* being adapted to fixedly adhere onto any point along the loop surface of the strap fastener profile 7 after the free end 72 of thereof passes though the buckle 71 and is turned backwardly to firmly fasten the strap fastener profile 7 at a final desired position.

Figure 13:
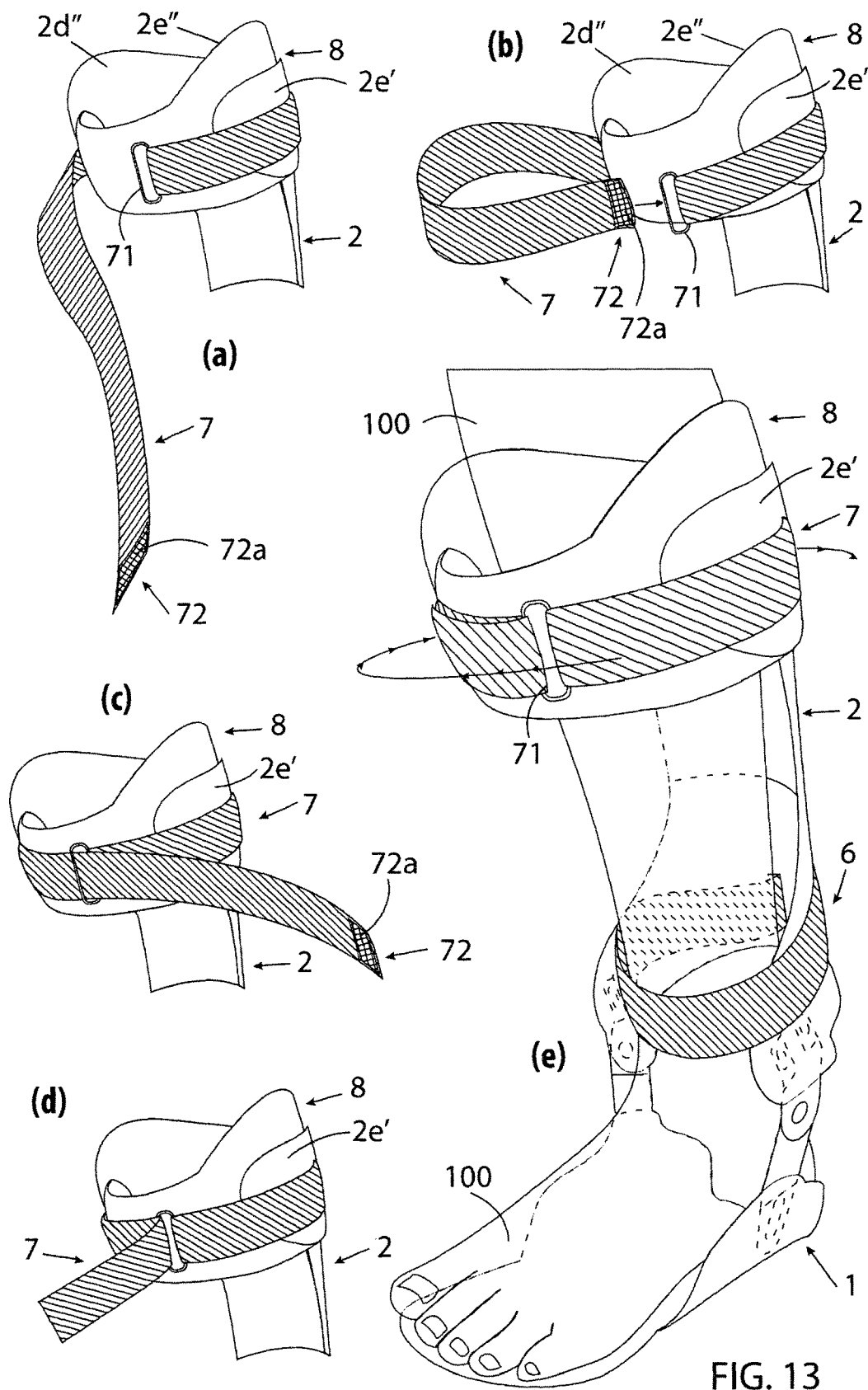
FIG. 13 shows sequential steps of positioning and fastening the upper strap fastener profile of the orthopedic brace of the invention as appropriate for a right-handed user.

With a scope of providing handy usage of the abovementioned upper strap fastener profile 7 of the calf covering portion 2 for right-handed users, the following sequential steps of positioning and fastening the same are presented in herein attached FIG. 13.

At first the user places the upper strap fastener profile 7 with the buckle 71 extending marginally forwardly the inner flange 2*e* of the calf covering portion 2 or of the covering flange 2*e*' of the textile patch 8 and pulls the same circumferentially around the rear exterior surface of either the calf covering portion 2 or of the textile patch 8 covering the same so that the strap fastener profile 7 might fixedly adhere onto the hooked strip surface 70 of the calf covering portion 2 or of the textile patch 8, whereby the free end 72 of the strap fastener profile will extend forwardly the flange 2*d* of the calf covering portion 2 or the flange 2*d*' of the textile patch 8 covering the same (FIG. 13*a*).

Thereafter the strap fastener profile 7 is pulled to bring the free end 72 thereof in the proximity of the buckle 71 (FIG. 13*b*), the free end 72 is passed through the buckle (FIG. 13*c*) and is further pulled and tensioned with a scope of desirably tightening it around the leg 100 of the user (FIG. 13*d*), the strap thereby forming a full circle around the leg 100 of the user. Subsequently the strap fastener profile length extending beyond the buckle 71 is rotated in an anticlockwise direction so that the end hooked surface portion 72*a* thereof abuts and is fixedly connected to the underlying loop surface of strap 7 after having been desirably tightened around the leg 100 of the user (FIG. 13*e*).

Figure 14:
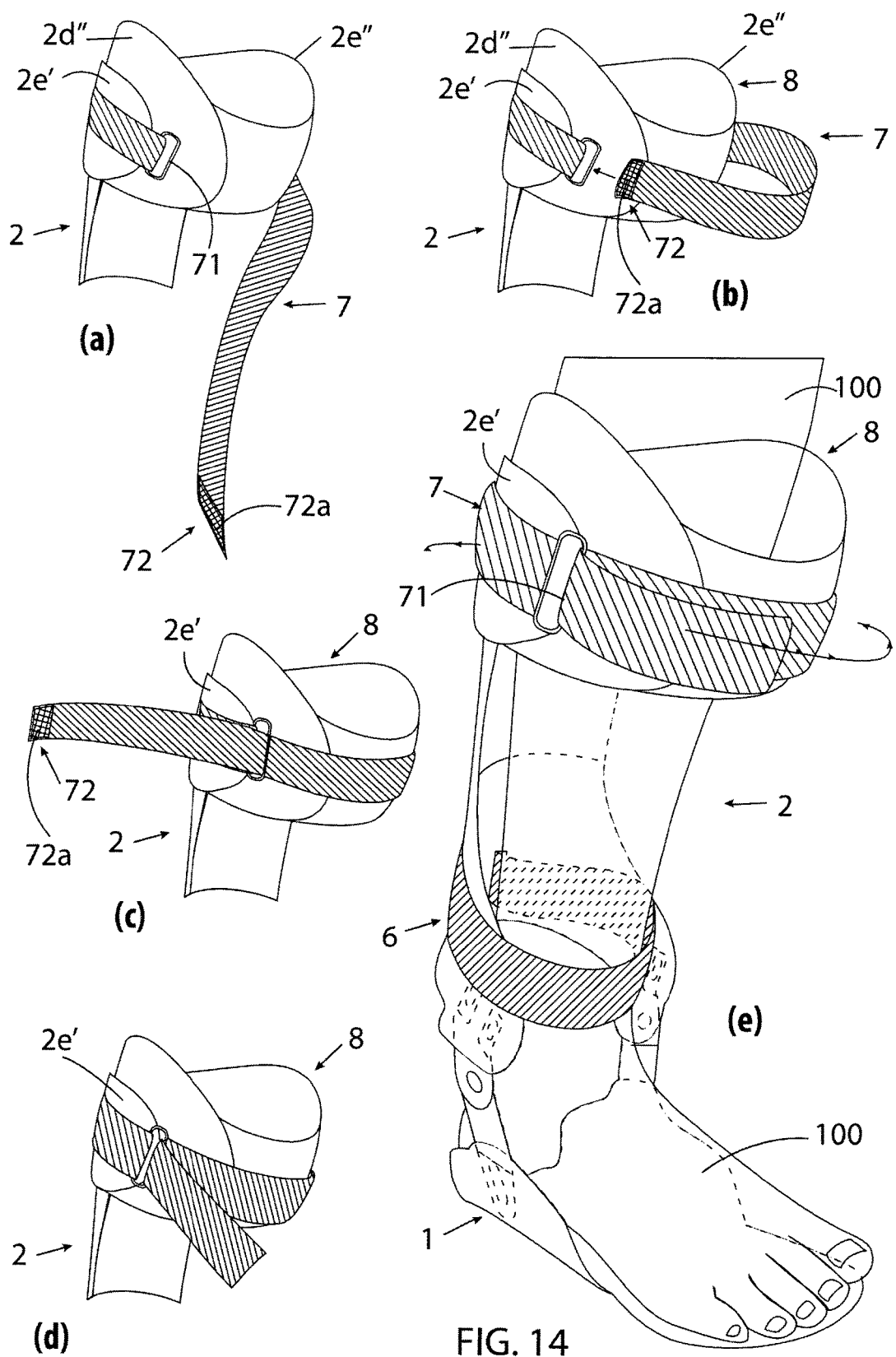
FIG. 14 shows sequential steps of positioning and fastening the upper strap fastener profile of the orthopedic brace of the invention as appropriate for a left-handed user.

Alternatively, with a scope of providing handy usage of the abovementioned upper strap fastener profile 7 of the calf covering portion 2 for left-handed users, the following sequential steps of positioning and fastening the same, identical with the steps followed hereinabove in the case of right-handed users with certain minor differences, are presented in herein attached FIG. 14.

At first the user places the upper strap fastener profile 7 with the buckle 71 extending marginally forwardly the inner flange 2*d* of the calf covering portion 2 or of the covering flange 2*d*' of the textile patch 8 and pulls the same circumferentially around the rear exterior surface of either the calf covering portion 2 or of the textile patch 8 covering the same so that the strap fastener profile 7 might fixedly adhere onto the hooked strip surface 70 of the calf covering portion 2 or of the textile patch 8, whereby the free end 72 of the strap fastener profile will extend forwardly the flange 2*e* of the calf covering portion 2 or the flange 2*e*' of the textile patch 8 covering the same (FIG. 14*a*).

Thereafter the strap fastener profile 7 is pulled to bring the free end 72 thereof in the proximity of the buckle 71 (FIG. 14*b*), the free end 72 is passed through the buckle (FIG. 14*c*) and is further pulled and tensioned with a scope of desirably tightening it around the leg 100 of the user (FIG. 14*d*), the strap thereby forming a full circle around the leg 100 of the user. Subsequently the strap fastener profile length extending beyond the buckle 71 is rotated in a clockwise direction so that the end hooked surface portion 72*a* thereof abuts and is fixedly connected to the underlying loop surface of strap 7 after having been desirably tightened around the leg 100 of the user (FIG. 14*e*).

The orthopaedic brace of the invention adapted to provide assistance to drop foot patients, offered as an AFO (FIG. 1) and/or a KAFO (FIG. 15) product is advantageous in that it is a ready to wear, try and purchase product, it is an optimally light weight and low cost product, whilst remaining fully efficient in providing dorsiflexion assistance to the foot of the wearer drop foot patient and it is discrete, not easily observable even by an attentive observer since it may be worn with ordinary shoes of all kinds.

While the invention has hereinabove been described by reference to various preferred embodiments, it is to be appreciated that these are for illustrative purposes only and that those skilled in the art will realize that changes and modifications may be made thereto without departing from the spirit of the invention; it is therefore intended to include such changes and modifications falling within the scope of the invention.

The invention claimed is:

1. An orthopedic brace adapted to provide foot raising assistance for drop foot comprising a foot base portion (1) and a calf covering portion (2), said foot base portion (1) comprising a sole portion (1c) and upwardly extending side flanges (1a, 1b) at a rear of the sides thereof, a pair of sole-raising hinge assemblies employed to pivotally connect said calf covering portion (2) to said foot base portion (1), each sole-raising hinge assembly comprising a vertically upwardly oriented first metallic strip member (3, 3') fixedly connected to each one of said upwardly extending side flanges (1a, 1b) of the foot base portion (1) and a second metallic plate member (4) fixedly connected to each flange of overlying bottom side flanges (2a, 2b) of the calf covering portion (2), a free end of said first metallic strip member (3, 3') provided with a hole (30) and a free end of said second metallic plate member (4) provided with a hole (40), a bolt connector (5) passing through aligned said hole (30) of said first metallic strip member (3, 3') and said hole (40) of said second metallic plate member (4), whereby said first metallic strip member (3, 3') and said second metallic plate member (4) of the hinge assembly are pivotally connected, wherein said first metallic strip member (3, 3') of the hinge assembly is provided with a lower portion that is embedded within said upwardly extending flanges (1a, 1b) of said foot base portion (1) during an injection thermosetting process of making the same and an upper portion extending vertically upwardly said flanges (1a, 1b), said lower portion provided with one or more openings (31) filled with plastic material that thoroughly covers said lower portion of said first metallic strip member (3, 3') during the injection thermosetting process of manufacturing said foot base portion (1);

said calf covering portion (2) comprising a curved elongate member (2c) that is adapted to extend from the region proximate to the foot up to the region proximate to the knee of the user with a pair of bottom side flanges (2a, 2b) and a pair of upper side flanges (2e, 2d), said elongate member (2c) comprising a central elongate vertically oriented aperture (20) located proximately the bottom thereof, the exterior surface of said calf covering portion (2) provided with hooked strip surfaces (60a, 60b) and with a hooked strip surface (70), said hooked strip surfaces (60a, 60b) located proximately the bottom of said calf covering portion (2) on either side of said central elongate vertically oriented aperture (20) and adapted to provide attachment of the ends of a strap fastener profile (6) having a loop texture and adapted to either fasten the calf covering portion (2) proximally to the bottom thereof onto the leg of the user or fasten the same with an additional function of providing correction of structural misalignment of the foot of the user of either the varus or the valgus type and said hooked strip surface (70) located proximally to the top of said calf covering portion (2) and adapted to provide attachment of a strap fastener profile (7) having a loop texture and adapted to fasten the calf covering portion (2) proximally to the top thereof onto the leg of the user; and wherein said second metallic plate member (4) of each sole-raising hinge assembly further comprises a pair of parallel plates (42), said pair of parallel plates (42) extending downwardly beyond the flanges (2a, 2b) of the calf covering portion (2) provided with coaxially oriented holes (40) and adapted to receive the upper portion of the first metallic strip members (3, 3') within a gap provided in between the pair of parallel plates, whereby said hole (30) at the free end of each one of the first metallic strip members (3, 3') is brought in alignment with said coaxially oriented holes (40) of said parallel plates (42), an upper portion of said second metallic plate member (4) provided with a rectilinear member (44) with an axial tubular housing (44a) adapted to receive an elongate compression spring (45), said compression spring (45) seated onto a base member (46) first introduced into the tubular housing (44a) and delimited by a bolt member (47) that serves as a top cover of the tubular housing (44a), said bolt member (47) variably screwed within the tubular housing (44a) so as to effect a variable tension of said elongate compression spring (45), a pair of identical side flange extensions (43) provided on either side of said rectilinear member (44) of the second metallic plate member (4), said side flange extensions (43) employed to connect said metallic plate member (4) onto said flanges (2a, 2b) of the calf covering portion (2).

2. The orthopedic brace of claim 1, wherein the orthopedic brace is provided ready to wear within ordinary shoes of any type in variable sizes adapted to fit a variety of shoe and leg sizes of individual users with progressively and proportionally increasing dimension parameters ($L_1$, $Z_1$, $W_1$) of the foot base portion (1) and correspondingly progressively and proportionally increasing dimension parameters ($L_2$, $Y_2$, $W_2$) of the calf covering portion (2), wherein ($L_1$) represents a distance of the rear to the frontal end of the sole base portion (1c), ($Z_1$) represents a distance of the hole (30) from the rear end of the sole base portion (1c), ($W_1$) represents a distance between the upwardly oriented lateral flanges (1a, 1b) of the foot base portion (1), ($L_2$) represents a distance of the bottom to the top of the calf covering portion (2) measured in the longitudinal direction of the leg of the user, ($Y_2$) represents a distance of the rear of the calf covering portion (2) from the frontal ends of the pair of upper side flanges (2e, 2d) thereof, and ($W_2$) represents a distance between the forwardly oriented lateral flanges (2a, 2b) of the calf covering portion (2).

3. The orthopedic brace of claim 2, wherein a dimension parameter ($h_1$) representing a distance of the sole base portion (1c) from the hole (30) of said first metallic strip members (3, 3') is maintained constant in said distinct sizes of the orthopedic brace with progressively and proportionally increasing the dimension parameters ($L_1$, $Z_1$, $W_1$) of the foot base portion (1) and correspondingly progressively and proportionally increasing the dimension parameters ($L_2$, $Y_2$, $W_2$) of the calf covering portion (2).

4. The orthopedic brace of claim 2, wherein a dimension parameter ($h_1$) representing a distance of the sole base portion (1c) from the hole (30) of said first metallic strip members (3, 3') is progressively and proportionally increased in said distinct sizes of the orthopedic brace with progressively and proportionally increasing the dimension parameters ($L_1$, $Z_1$, $W_1$) of the foot base portion (1) and correspondingly progressively and proportionally increasing the dimension parameters ($L_2$, $Y_2$, $W_2$) of the calf covering portion (2).

5. The orthopedic brace of claim 1, wherein a pair of distinct items of said first metallic strip member (3, 3') are employed in association with the upwardly raised side flanges (1b, 1a) of the foot base portion (1) respectively to appropriately adapt to the configuration of corresponding malleolus medialis and malleolus lateralis of individual users, and one of the pair of distinct items of said first metallic strip member (3, 3') is a planar strip, and an other of the pair of distinct items of said first metallic strip member (3, 3') is a planar strip bent outwardly at an intermediate bend (32) upwardly said lateral flange (1a) of the foot base portion thereby appropriately providing for the protruding configuration of the ankle.

6. The orthopedic brace of claim 1, wherein said side flange extensions (43) of the second metallic plate member (4) of the hinge assembly are provided with holes (41') adapted to receive bolts (51) for fixedly securing said metallic plate member (4) onto the flanges (2a, 2b) of the calf covering portion (2).

7. The orthopedic brace of claim 1, wherein said side flange extensions (43) of the second metallic plate member (4) of the hinge assembly are provided with an array of apertures (41), said apertures (41) filled with plastic raw material during a thermosetting injection process of industrial production of the calf covering portion (2), whereby said metallic plate members (4) are embedded and fixedly held within said flanges (2a, 2b) of the calf covering portion (2).

8. The orthopedic brace of claim 1, wherein the orthopedic brace is an ankle-foot orthosis (AFO) product comprising said foot base portion (1) and said calf covering portion (2) and the orthopedic brace is adapted to be fastened onto the leg (100) of the user with a lower strap fastener profile (6) adapted to surround the leg of the user and attached onto said hooked strip surfaces (60a, 60b) proximally to the bottom of the exterior surface of the calf covering portion (2) and with said strap fastener profile (7) adapted to surround the leg (100) of the user and attached onto said hooked strip surface (70) proximally to the top of the exterior surface of the calf covering portion (2).

9. The orthopedic brace of claim 8, wherein one end of said strap fastener profile (6) is fixedly attached onto one of the pair of said hooked strip surfaces (60a, 60b), and a free end of said strap fastener profile (6) is adapted to be turned encircling the entire said calf covering portion (2) with the leg of the user therein and is fixedly attached onto the other one of the pair of said hooked strip surfaces (60a, 60b) at the rear exterior surface of the calf covering portion (2).

10. The orthopedic brace of claim 8, wherein said strap fastener profile (6) adapted to be employed as a fastener for fastening the calf covering portion (2) proximally to the bottom thereof onto the leg of the user additionally adapted to provide correction of structural misalignment of the foot of the user of either the varus or the valgus type, wherein one end of said strap fastener profile (6) passes through said central elongate vertically oriented aperture (20) of the calf covering portion (2) and is fixedly attached onto one of the pair of said hooked strip surfaces (60a, 60b), a free end of said strap fastener profile (6) is adapted to be turned in a clockwise direction encircling the leg of the user in a varus type structural misalignment of the foot of the user and in an anticlockwise direction encircling the leg of the user in a valgus type structural misalignment of the foot of the user without encircling the entire said calf covering portion (2) and is fixedly attached onto the other one of the pair of said hooked strip surfaces (60a, 60b) at the rear exterior surface of the calf covering portion (2).

11. The orthopedic brace of claim 1, wherein the orthopedic brace is a knee-ankle-foot orthosis (KAFO) product, further comprising a femur covering portion (200) that extends upwardly from said calf covering portion (2), said femur covering portion (200) connected to said calf covering portion (2) by bilaterally disposed metallic members (230), said metallic members (230) fixedly secured onto the sides of said calf covering portion (2) and pivotally connected to bilaterally disposed metallic plate members (240) fixedly connected at the sides of said femur covering portion (200), wherein a lower strap fastener profile (260) and an upper fastener profile (270) are adapted to securely fasten said femur covering portion (200) along a femur of the user.

12. The orthopedic brace of claim 11, wherein said strap fastener profile (6) adapted to be employed as a fastener for fastening the calf covering portion (2) proximally to the bottom thereof onto the leg of the user additionally adapted to provide correction of structural misalignment of the foot of the user of either the varus or the valgus type, wherein one end of said strap fastener profile (6) passes through said central elongate vertically oriented aperture (20) of the calf covering portion (2) and is fixedly attached onto one of the pair of said hooked strip surfaces (60a, 60b), a free end of said strap fastener profile (6) is adapted to be turned in a clockwise direction encircling the leg of the user in a varus type structural misalignment of the foot of the user and in an anticlockwise direction encircling the leg of the user in a valgus type structural misalignment of the foot of the user without encircling the entire said calf covering portion (2) and is fixedly attached onto the other one of the pair of said hooked strip surfaces (60a, 60b) at the rear exterior surface of the calf covering portion (2).

13. The orthopedic brace of claim 11, wherein one end of said strap fastener profile (6) is fixedly attached onto one of the pair of said hooked strip surfaces (60a, 60b), a free end of said strap fastener profile (6) is adapted to be turned encircling the entire said calf covering portion (2) with the leg of the user therein and is fixedly attached onto the other one of the pair of said hooked strip surfaces (60a, 60b) at the rear exterior surface of the calf covering portion (2).

* * * * *